US007148405B2

(12) United States Patent
Mok et al.

(10) Patent No.: US 7,148,405 B2
(45) Date of Patent: Dec. 12, 2006

(54) **ENZYMES RESPONSIBLE FOR THE METABOLISM OF *CIS*-ZEATIN**

(75) Inventors: David W. S. Mok, Corvallis, OR (US);
Machteld C. Mok, Corvallis, OR (US);
Ruth C. Martin, Corvallis, OR (US);
Jeffrey E. Habben, Urbandale, IA (US)

(73) Assignees: State of Oregon Acting by and through the State Board of Higher Education on behalf of Oregon State University, Corvallis, OR (US);
Pioneer Hi-Bred International, Inc., Johnston, IA (US)

( * ) Notice: Subject to any disclaimer, the term of this patent is extended or adjusted under 35 U.S.C. 154(b) by 293 days.

(21) Appl. No.: 10/275,782

(22) PCT Filed: Jun. 5, 2001

(86) PCT No.: PCT/US01/18406

§ 371 (c)(1),
(2), (4) Date: Nov. 8, 2002

(87) PCT Pub. No.: WO01/94564

PCT Pub. Date: Dec. 13, 2001

(65) Prior Publication Data

US 2003/0213018 A1 Nov. 13, 2003

Related U.S. Application Data

(60) Provisional application No. 60/209,842, filed on Jun. 6, 2000.

(51) Int. Cl.
*C12N 15/29* (2006.01)
*C12N 15/82* (2006.01)
*A01H 5/00* (2006.01)

(52) U.S. Cl. .................. 800/298; 536/23.6; 536/23.1; 435/320.1

(58) Field of Classification Search ............... 536/23.1, 536/23.6, 24.1; 435/320.1, 468; 800/298, 800/278, 287
See application file for complete search history.

(56) References Cited

FOREIGN PATENT DOCUMENTS

WO  WO 99/06571   2/1999
WO  WO 99/51758  * 10/1999

OTHER PUBLICATIONS

Roeckel et al (1997, Transgenic Research 6(2):133-141).*
Sa et al (2002. Transgenic Research 11(3):269-278).*
Bowie et al, Science 247:1306-1310, 1990.*
McConnell et al, Nature 411 (6838):709-713, 2001.*
Fourgoux-Nicol et al (1999, Plant Molecular Biology 40 :857-872).*

Dietrich and Morris, "Isolation of Stage-Specific Transcripts from Developing Maize Endosperm," *Plant Physiol.* 99(1 Supp):31, 1992.
Dixon et al., "Zeatin Glycosylation Enzymes in *Phaseolus*," *Plant Physiol.* 90:1316-1321, 1989.
Hocart et al., "Cytokinins of dry Zea-mays seed quantification by radioimmunoassay and gas chromatography-mass spectrometry," *J. Plant Growth Reg.* 7(3):179-196, 1988 (abstract only).
Horvath et al., "Identification of an immediate-early salicylic acid-inducible tobacco gene and characterization of induction by other compounds," *Plant Mol. Biol.* 31:1061-1072, 1996.
Jameson, *Cytokinin Metabolism and Compartmentation. In: Cytokinins. Chemistry, Activity. and Function.* Mok et al., (eds.), CRC Press, Inc., pp. 113-128, 1994.
Letham et al., "O-glucosylzeatin and Related Compounds—A New Group of Cytokinin Metabolites," *Ann. Botany* 41:261-263, 1976.
Letham, "Zeatin, A Factor Inducing Cell Division Isolated from *Zea Mays*," *Life Sci.* 8:569-573, 1963.
Martin et al., "A Gene Encoding the Cytokinin Enzyme Zeatin ()-Xylosyltransferase of *Phaseolus vulgaris*," *Plant Physiol.* 120:553-557, Jun.1999.
Martin et al., "A maize cytokinin gene encoding an O-glucosyltransferase specific to cis-zeatin," *PNAS* 98(10):5922-5926, May 8, 2001.
Martin et al., "Monoclonal Antibody Specific to Zeatin O-Glycosyltransferases of *Phaseolus*," *Plant. Physiol.* 94:1290-1294, 1990.
Martin et al., "Isolation of a cytokinin gene, *ZOG1*, encoding zeatin O-glucosyltransferase from *Phaseolus lunatus*," *Proc. Natl. Acad. Sci USA* 96:284-289, Jan. 1999.
Martin et al., "Protein processing and auxin response in transgenic tobacco harboring a putative tobacco cDNA of zeatin O-xylosyltransferase from *Phaseolus vulgaris*," *Plant J.* 12(2):305-312, 1997.
Miller et al., "Kinetin, A Cell Division Factor From Deoxyribonucleic Acid," *J. American Chem. Soc*, 77: 1392, 1955.
Miller et al., "Isolation Structure and Synthesis of Kinetin, a Substance Promoting Cell Division," *J. American Chem. Soc.* 78:1375-1380, 1956.
Mok et al., (eds.), *Cytokinins and Plant Development—An Overview. In: Cytokinins, Chemistry, Activity. and Function.* Mok et al., (eds), CRC Press, Inc., Boca Raton, Florida, 1994.
Shaw and Wilson, "A Synthesis of Zeatin," *Proc. Chem. Soc.* p. 231, Jul. 1964.
Sugiyama and Hashizume, "Cytokinins in Developing Tuberous Roots of Sweet Potato," *Agric. Biol. Chem.*53(1):49-52, 1989.
GenBank Accession No. AU031046, "Oryza sativa (japonica cultivar-group) cDNA, partial sequence (E60679_6z)," Oct. 16, 1998.

(Continued)

*Primary Examiner*—Stuart F. Baum
(74) *Attorney, Agent, or Firm*—Klarquist Sparkman, LLP

(57) ABSTRACT

Isolated nucleic acids encoding cis-zeatin O-glucosyltransferase are disclosed. These nucleic acid molecules are useful, among other things, to produce transgenic plants having modified cis-zeatin O-glucosyltransferase activity and/or modified growth and developmental patterns.

5 Claims, 5 Drawing Sheets

OTHER PUBLICATIONS

GenBank Accession No. AF116858.1, "Phaseolus vulgaris zeation O-xylosyltransferase (ZOX1) gene. complete cds." Sep. 1, 1999.

GenBank Accession No. AW065903, "687002F11.y1 687—Early embryo from Delaware Zea mays cDNA, mRNA sequence," Oct. 18, 1999.

GenBank Accession No. AQ867816, "nbeb003M20f CUGI Rice BAC Library (EcoR1) Oryza sativa genomic clone nbeb003M20f, genomic survey sequence (TMH-Please Verify Format)," Nov. 9, 1999.

GenBank Accession No. AF318075, "Zea mays cis-zeatin O-glucosyltransferase (ciszog1) mRNA, complete cds.," May 17, 2001.

* cited by examiner

FIGURE 4

| | | | |
|---|---|---|---|
| Gap Weight: | 50 | Average Match: | 10.000 |
| Length Weight: | 3 | Average Mismatch: | -9.000 |
| Quality: | 875 | Length: | 394 |
| Ratio: | 2.238 | Gaps: | 2 |
| Percent Similarity: | 60.614 | Percent Identity: | 60.614 |

Match display thresholds for the alignment(s):
  | = IDENTITY
  : = 5
  . = 1

ZOG1-orf.seq x cis-ZOG1-orf.seq..

```
 743 GGCACCCATGCATGGAGTGGCTTGATAAACAAGAGCCAAGTTCAGTCATA  792
     |||||   |||  |||||||||| ||  ||    |||     || ||   |
 764 GGCACGAGTGCCTGGAGTGGCTCGACAGGCAGCCGCCGGAGTCGGTGCTC  813

793 TATATATCCTTCGGGACCACGACAGCTTTGAGAGATGAACAAATCCAACA  842
     ||   |  || |||||  || ||  |          |    |  ||| || |
 814 TACGTCTCGTTCGGAACGACTTCGTGCCTCCACGCCGACCAAGTCGCCGA  863

843 GATAGCAACTGGGTTGGAACAAAGCAAGCAGAAGTTCATCTGGGTGCTGA  892
     |  ||  | | | |  |      ||||||||||   ||| ||||||||||
 864 GCTCGCCGCGGCGCTCAAGGGCAGCAAGCAGCGTTTCGTCTGGGTGCTGC  913

893 GAGAAGCCGATAAAGGGGACATCTTTGCCGGAAGTGAAGCAAAAAGGTAT  942
     |  || |||||      |  |||||| |   ||||     |   |   || |
 914 GCGACGCCGACCGCGCCGACATATACGCCGAGTCCGGCGAGAGCCGGCAC  963

943 G..AACTTCCAAAGGGTTTTGAGGAGAGAG.TGGAAGGAATGGGGCTGGT  989
     |   |  ||||      |  || |  || |||   || || | |||||||||
 964 GCCATGTTCCTGTCCGAGTTCACCAGGGAGACCGAGGGCACGGGGCTGGT  1013

990 TGTGAGGGACTGGGCACCCCAATTGGAAATTCTGAGCCACAGTTCAACAG  1039
      | |  |   |||||  || || || ||||  || |||    |||  | || |
1014 CATCACCGGGTGGGCGCCGCAGCTGGAGATCCTGGCGCACGGCGCCACGG  1063

1040 GGGGGTTTATGAGCCATTGTGGATGGAACTCGTGCTTGGAGAGCATAACC  1089
     ||  ||  ||||||||  || || ||||||||||  |  |||||| | | |
1064 CGGCCTTCATGAGCCACTGCGGCTGGAACTCGACCATCGAGAGCCTGAGC  1113

1090 ATGGGGGTGCCAATAGCAACATGGCCCATGCACTCTGACCAGCC  1133
     |||   |||   |   |   ||||||||||||||| ||||||||
1114 CACGGGAAGCCGGTGCTTGCCTGGCCCATGCACTCCGACCAGCC  1157
```

FIGURE 5

```
BESTFIT  Gap Weight:         8    Average Match:     2.912
         Length Weight:      2    Average Mismatch: -2.003
               Quality:    851           Length:      463
                 Ratio:  1.908             Gaps:       11
     Percent Similarity: 52.489   Percent Identity:  40.724
         Match display thresholds for the alignment(s):
                          | = IDENTITY
                          : = 2
                          . = 1
```

*zog1*-orf.pep x *cisZOG1*-orf.pep

```
 14 VVVLLIPFPAQGHLNQFLHLSRLIVAQNIPVHYVGTVTHIRQATLRYN..  61
    | |.:||||||||||| ||||  |:  .. : |||      |:|||  | .
  9 VAVVAVPFPAQGHLNQLLHLSLLLASRGLSVHYAAPPPHVRQARARVHGW  58

62 NPTS..NIHFHAFQVPPFVSPPPN..PEDDFPSHLIPSFEA.SAHLREPV 106
    .|  . .| ||   |||: || |.        ||.||.| ||| .|  | |.
 59 DPRALGSIRFHDLDVPPYDSPAPDLAAPSPFPNHLMPMFEAFAAAARAPL 108

107 GKLLQSLSSQAKRVVVINDSLMASVAQDAANISNVENYTFHSFSAFNTSG 156
    ||| ||. :|| |: | |     | :|| :.| : :  .       |
109 AALLQRLSTSYRRVAVVFDRLNPFAATEAARLANADAFGLQCVAISYNVG 158

157 DFWEEMGKPPVGDFHFPEFPSLEGCIAAQFKG..FRTAQYEFRKFNNGDI 204
    | : |  . |:      |  : |.. :|    ||    : |        | :
159 ..WLDPGHRLLSDYGLQFLPP.DACMSREFVDLVFRMEEEQGAPVAGLV 205

205 YNTSRVIEGPYVELLEL...FNGGKKVWALGPFNPLAVEKKDSI....GF 247
    || | :|| :.:..      |  |.: .|.|| |||  .:
206 MNTCRALEGEFLDVVAAQPPFQ.GQRFFAVGPLNPLLLDADAPTTPPGQA 254

248 RHPCMEWLDKQEPSSVIYISFGTTTALRDEQIQQIATGLEQSKQKFIWVL 297
    || |:||||:|  | ||:|:||||.  |  :|: ::|  |. |||:|:|||
255 RHECLEWLDRQPPESVLYVSFGTTSCLHADQVAELAAALKGSKQRFWVL 304

298 READKGDIFAGSEAKRYEL.PKGFEERVEGMGLVVRDWAPQLEILSHSST 346
    |:||: ||:| |  |: :   |     ||  |||:  ||||||||.| .|
305 RDADRADIYAESGESRHAMFLSEFTRETEGTGLVITGWAPQLEILAHGAT 354

347 GGFMSHCGWNSCLESITMGVPIATWPMHSDQPRNAVLVTEVLKVGLVVKD 396
    ||||||||| :||:. | |: |||||||| ..|..  | ||.|:
355 AAFMSHCGWNSTIESLSHGKPVLAWPMHSDQPWDSELLCKYFKAGLLVRP 404

397 WAQRNSLVSASVVENGVRRLMETKEGDEMRQRAVRLKNAIHRSMDEGGVS 446
    |  . :| |  :: :     |. |  .|||| |  |:  |. :|| |
405 WEKHAEIVPAQAIQKVIEEAMLSDSGMAVRQRAKELGEAVRASVADGGNS 454

447 HMEMGSFIAHISK 459
    ::   ||  :|.:
455 RKDLDDFIGYITR 467
```

ENZYMES RESPONSIBLE FOR THE METABOLISM OF CIS-ZEATIN

CROSS REFERENCE TO RELATED APPLICATIONS

This is the U.S. National Stage of International Application No. PCT/US01/18406, filed Jun. 5, 2001, which was published in English under PCT Article 21(2), which in turn claims the benefit of U.S. Provisional Application No. 60/209,842, filed Jun. 6, 2000. Both applications are incorporated herein in their entirety.

FIELD OF THE DISCLOSURE

This disclosure relates to plant hormones and in particular to cytokinins. Aspects of the disclosure include a purified cis-zeatin O-glucosyltransferase enzyme, nucleic acid molecules encoding this enzyme, and vectors containing all or a portion of the nucleic acid molecule. Transgenic cells and transgenic plants having modified cis-zeatin O-glucosyltransferase activity are also provided. The disclosure also relates to altered plant traits in general, and seed development and yield in particular, resulting from the modification of cis-zeatin O-glucosyltransferase activity in plants.

BACKGROUND

Cytokinins are plant hormones that mediate cell division and development. This group of hormones was discovered by Miller et al. (Miller et al., *Journal of American Chemical Society* 77:1392, 1955; Miller et al., *Journal of American Chemical Society* 78:1375–1380, 1956) with the identification of the first synthetic cytokinin, kinetin. The first naturally occurring cytokinin, zeatin (trans-zeatin), was discovered by Letham (Letham et al., *Ann. Botany* 41:261–263, 1976) in corn, and the structure of zeatin was determined by Shaw and Wilson (Shaw et al., *Proceedings of Chemical Society* 231, 1964). Zeatin is the most active and ubiquitous cytokinin in all plant species examined to date. Other naturally occurring cytokinins are structurally related to zeatin (Shaw, *Cytokinins, Chemistry, Activity and Function*, Mok and Mok, CRC Press, 15–34, 1994).

The critical importance of cytokinins in plant development was illustrated by the classic tissue culture experiments of Skoog et al. (Skoog et al., *Science* 148:532, 1965). These experiments established that plant cell division requires cytokinin. Furthermore, the ratio of cytokinins to auxins (another group of plant hormones) was shown to indicate whether undifferentiated plant cells would develop into shoots (high cytokinin to auxin) or roots (low cytokinin to auxin), or continue to proliferate as callus tissues (intermediate cytokinin to auxin ratio). Thereafter, cytokinin was found to be involved in every phase of plant growth (Mok, *Cytokinins, Chemistry, Activity and Function*, Mok and Mok, CRC Press, 155–166, 1994). In general, cytokinins have growth promoting effects, from seed germination and shoot development to retarding senescence and increasing fruit and seed set The effects of cytokinins in controlling plant growth have been extensively utilized in plant tissue culture to micropropagate and clone plants and to regenerate whole plants from cells of many species (Krikorian, *Plant Hormones-Physiology, Biochemistry and Molecular Biology*, 2$^{nd}$ Edition, Davies, Kluwer Academic Publishers, 774–796, 1995). In fact, the application of cytokinins in vitro contributes significantly to advances in plant biotechnology. In agricultural applications, external applications of cytokinins on whole plants are used to obtain enhanced fruit set and gram yield of food crops and longer shelf life of ornamentals (Hradecka et al., *Physiology and Biochemistry of Cytokinins in Plants*, Kaminek et al., SPB Academic Publishing, 245–247, 1992; Karanov et al., *Progress in Plant Growth Regulation*, Karssen et al., 842–851, 1992; Lewis et al., *Physiol. Plant.* 98:187–195, 1996; Minana et al., *J. Exp. Bot.* 219:1127–1134, 1989).

In whole plants, cytokinins are synthesized in the roots and transported to above ground parts (Letham, *Cytokinins: Chemistry, Activity and Function*, Mok, and Mok, CRC Press, Boca Raton, 57–80, 1994), although other actively growing tissues also have biosynthetic capacity. Two biosynthetic pathways have been proposed for cytokinin biosynthesis. The first is the direct pathway, involving formation of $N^6$-isopentenyladenosine phosphate from AMP and dimethylallyl pyrophosphate, followed by hydroxylation of the side chain to form zeatin-type compounds. The second pathway is the indirect pathway, in which cytokinins are released by turnover of tRNA containing cis-zeatin (Prinsen et al., *Plant Growth Regul.* 23:3–15, 1997). Plant AMP isopentenyltransferases have not been found in spite of the identification of such genes from bacteria such as *Agrobacterium tumefaciens* (Akiyoshi et al., *Proc. Natl. Acad. Sci. USA* 81:5994–5998, 1984; Barry et al., *Proc. Natl. Acad. Sci.* 81:4776–4780, 1984; Beaty et al., *Mol. Gen. Genet.* 203:274–280, 1986). In fact, plant DNA homologous to these bacterial genes has not been reported. Therefore, the intermediates, the enzymes, and the genes involved in direct pathway(s) of cytokinin biosynthesis in plants remain unproven or unknown. Cytokinins occur adjacent to the anticodon in tRNAs recognizing codons beginning with U (Skoog et al., *Ann. Rev. Plant Physiol.* 21:359–384, 1970; Taller, *Cytokinins, Chemistiy, Activity and Function*, Mok and Mok, CRC Press, 101–112, 1994). The indirect pathway involves release of cytokinins from breakdown of such tRNA. Although the weakly active cis-zeatin is the major cytokinin in plant tRNA, cis-zeatin can be converted to trans-zeatin by cis-trans isomerization (Bassil et al., *Plant Physiol.* 102:867–872, 1993).

Although trans-zeatin and its derivatives are prevalent in most plants, cis-zeatin has been found in potato (Mauk et al., *Plant Physiol.* 62:438–442, 1978), tobacco (Tay et al., *Plant Sciences* 43:131–134, 1986), rice (Izumi et al., *Plant Cell Physiol.* 29:97–104, 1988), and as the predominant cytokinin in chickpeas (Emery et al., *Plant Physiol.* 117:1515–1523, 1998). Relatively high levels of cis-zeatin occurs in below-ground parts of the plants such as roots and tubers. Cones of hops (Watanabe et al., *Plant and Cell Physiol.* 22:489–500, 1981) and unisex flowers of *Mercurialis* (Durand et al., *Cytokinins, Chemistry, Activity and Function*, Mok and Mok, CRC Press, 295–304, 1994) also contain much cis-zeatin. Therefore, cis-zeatin may play a unique role in biosynthesis as well as in mediating specific developmental steps not yet discovered.

Cytokinins are converted to various metabolites in plant tissues (Jameson, *Cytokinins, Chemistry, Activity and Function*, Mok and Mok, CRC Press, 113–128, 1994). For example, the metabolites of zeatin include O-glycosylzeatin, N-glucosylzeatin, zeatin riboside, and zeatin nucleotides. The precise functions of these metabolites are still uncertain. However, some may be the stored or the transported form of the active compound, zeatin. O-Glucoside of zeatin (FIG. 1) may be such a metabolite (Badenoch-Jones et al., *Plant Cell and Environment* 19:504–516, 1996). Trans-Zeatin O-glucoside was first discovered by Letham et al. (Letham et al.,

*Ann. Botany* 41:261–263, 1976) and has been found in all crops examined including corn, beans, poplar, soybean, etc. As O-glucosylzeatin can be readily converted back to its active form, zeatin, by the removal of the glucose moiety (via the action: of wide-spread enzymes, β-glucosidases), O-glucosylzeatin is considered a reversible reserve of active cytoknin (Brzobohaty et al., *Science* 262:1051–1054, 1993). Also, O-glucosylzeatin is resistant to attack by cytokinin oxidases (McGaw et al., *Planta* 159:30–37, 1983) that degrade the parent compound, zeatin. Therefore, O-glucosylzeatin may be important in cytokinin action by serving as an interchangeable reserve and as an oxidase resistant form of zeatin. Another metabolite, zeatin O-xyloside was fist discovered in beans (Phaseolus) by Lee et al., (Lee et al., *Plant Physiol.* 77:635–641, 1985). Zeatin O-xyloside is also resistant to degradation and can be reconverted to zeatin. Two enzymes, zeatin O-glucosyltransferase (ZOG) and zeatin O-xylosyltransferase (ZOX), catalyzing the formation of zeatin to O-glucosylzeatin and O-xylosylzeatin, respectively, were first purified and characterized in the Mok laboratory (Turner et al., *Proc. Natl. Acad. Sci.* 84:3714–3717, 1987; Dixon et al., *Plant Physiology* 90:1316–1321, 1989). The occurrence of the enzymes is species specific. The former was isolated from lima beans (*Phaseolus lunatus*) and the latter from common beans (*P. vulgaris*). The isolation of the enzymes was followed by the generation of specific antibodies recognizing the enzymes (Martin et al., *Plant Physiology* 94:1290–1294, 1990). Subsequently, two genes encoding the respective enzymes were cloned (Martin et al., *Proc. Natl. Acad Sci. USA* 96:284–289, 1999; Martin et al., *Plant Physiol.* 120:553–557, 1999). The genes were designated as ZOG1 (for zeatin O-glucosyltransferase) and ZOX1 (for zeatin O-xylosyltransferase).

Plants having modified endogenous zeatin activity would be of significant agricultural importance. Such plants could be created through genetic engineering if the genes regulating zeatin were available. It is to such genes, and polypeptides encoded thereby, that the present disclosure is directed.

SUMMARY OF THE DISCLOSURE

The present disclosure provides isolated plant nucleic acid molecules (cDNA and ORF sequences) encoding cis-zeatin O-glucosyltransferase (cis-ZOG1), a key enzyme in the regulation of zeatin activity in plants.

In one embodiment, the cis-ZOG1 nucleic acids disclosed are from corn, *Zea mays*. The open reading frame of these nucleic acid molecules encodes a polypeptide of 467 amino acids in length. This polypeptide is shown to have cis-ZOG1 enzymatic activity i.e., the enzyme catalyzes the conversion of cis-zeatin to cis-O-glucosylzeatin. Accordingly, one aspect comprises isolated nucleic acid molecules encoding cis-ZOG1. Another aspect is the purified cis-ZOG1 enzyme, and fragments and variants thereof that maintain substantial (e.g., greater than 50% of the native protein) catalytic activity.

Also encompassed within the scope of this disclosure are transformation vectors that include at least a portion of the disclosed nucleic acid sequences. Such vectors may be transformed into plants to produce transgenic plants having modified cis-ZOG1 activity. Depending on the particular sequence incorporated into the vector, transformation with the cis-ZOG1 cDNA, genes, or derivatives thereof may be used to modify agronomically important traits, including the activity of zeatin in seeds, grain yield, seed germination rates, and plant growth. While all crop plants may benefit from such modified activity, it is believed that the disclosure will be particularly valuable in *Zea mays*, wheat, rice, potato, and legumes.

Typically, vectors used to modify cis-ZOG1 activity include regulatory sequences that are operably linked to the cis-ZOG1 cDNA, ORF, or derivatives thereof. For example, cis-ZOG1 activity may be modified in plants by introducing a transformation vector that includes a sense or antisense form of the disclosed cDNA operably linked to a high-level constitutive promoter such as the 35S promoter of cauliflower mosaic virus. Transgenic plants tansformed with such recombinant vectors and having modified cis-ZOG1 activity are part of the disclosure.

The disclosure provides cis-ZOG1-encoding nucleic acids from *Zea mays*, and it additionally encompasses homologs, orthologs and derivatives of these sequences, as well as homologs, orthologs, and variants of the cis-ZOG1 polypeptide sequence. Thus, according to one aspect of the disclosure, nucleic acid molecules that comprise specified regions of these sequences are provided. Exemplary of such nucleic acid molecules are oligonucleotides that are useful as probes or primers to detect and amplify cis-ZOG1-encoding nucleic acids from other plant species. Such oligonucleotides are useful as hybridization probes or PCR primers, and typically comprise at least 15 consecutive bases of the disclosed sequences. In other embodiments, such oligonucleotides comprise longer regions of the disclosed sequences, such as at least 20, 25 or 30 consecutive nucleotides.

In another aspect, the disclosure provides compositions and methods for isolating nucleic acid sequences having cis-ZOG1 activity from other plant species. Typically, such methods involve hybridizing probes or primers derived from the disclosed *Zea mays* sequences to nucleic acids obtained or derived from such other plant species.

Homologous and orthologous sequences to the *Zea mays* cis-ZOG1 nucleic acid and amino acid sequences share key functional and structural characteristics with the disclosed *Zea mays* sequences. Functionally, such sequences encode (or comprise) a polypeptide that catalyzes the O-glucosylation of cis-zeatin. Structurally, such sequences share a specified structural relationship with the disclosed sequences. By way of example, in certain embodiments, homologous amino acid sequences have at least 70% sequence identity with the *Zea mays* cis-ZOG1 amino acid sequence. In other embodiments, homologous nucleic acid sequences hybridize under stringent conditions to the disclosed *Zea mays* cis-ZOG1 nucleic acid sequences.

Another aspect of the disclosure provides purified cis-ZOG1 enzyme. Having provided nucleic acid molecules that encode these enzymes, the disclosure facilitates the expression of cis-ZOG1 in heterologous systems, including, but not limited to, *E. coli*, yeast, and baculovirus expression systems. Thus, the disclosure permits the large-scale production of the enzymes for agricultural and other applications.

These and other aspects of the disclosure will become readily apparent in light of the following detailed description.

BRIEF DESCRIPTION OF THE DRAWINGS

FIG. 2A shows the elution profile of the cis-zeatin standard. FIG. 2B shows the elution profile of products from a reaction with $^{14}$C-cis-zeatin, recombinant cis-zeatin-O-glucosyltransferase, and uridine diphosphate glucose (UDPG). FIG. 2C shows the elution profile of reaction products with cis-zeatin after digestion with β-glucosidase.

Figure 2:
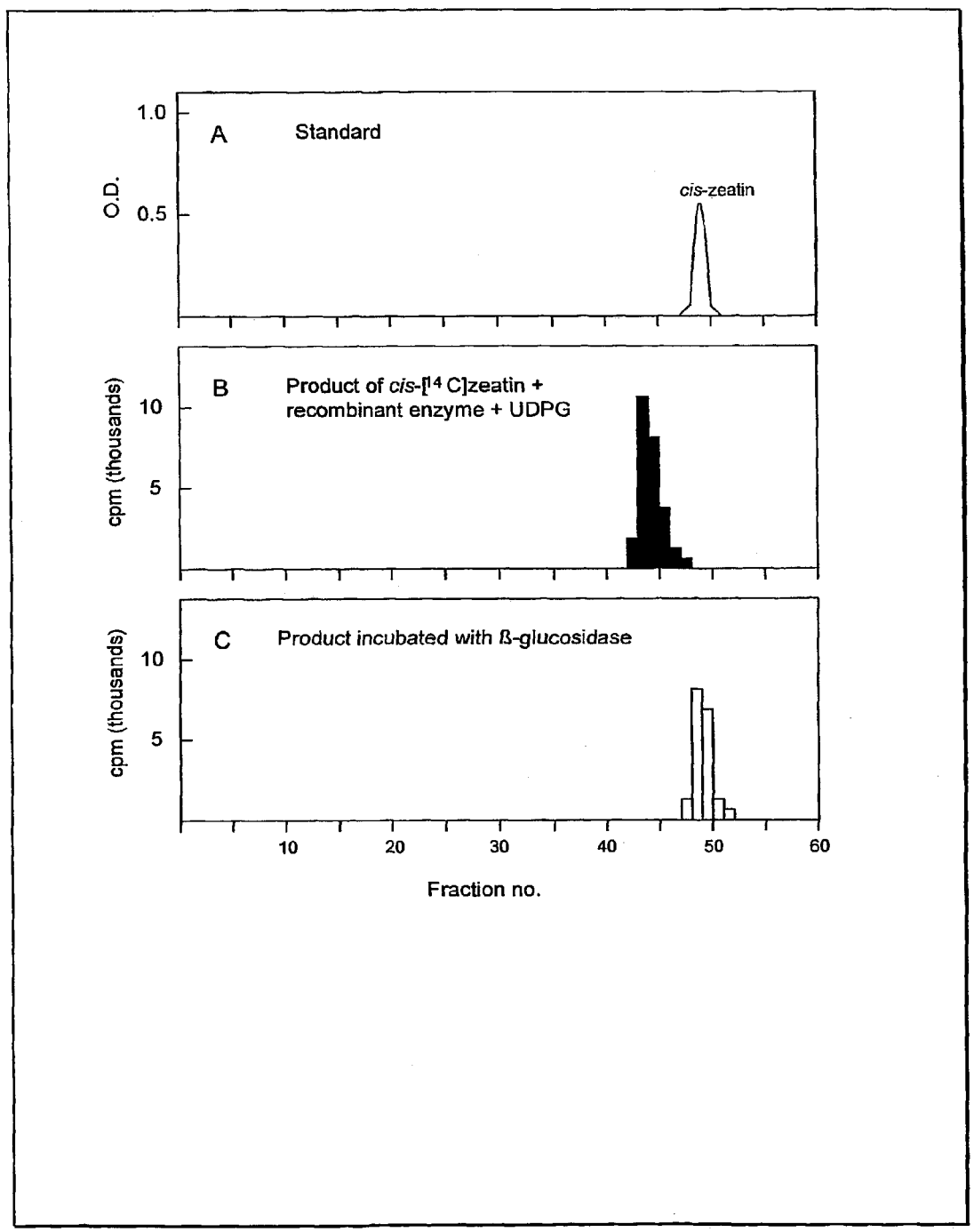
FIG. 2 is a series of graphs showing the analysis of enzymatic reaction products by HPLC.

For FIG. 2B, 200 μL of supernatant obtained from cell culture was incubated with approximately 1 nmol of labeled zeatin and UDPG for 2 hours. For FIG. 2C, Approximately 0.4 nmole of reaction product obtained from reactions similar to FIG. 2B was incubated with β-glucosidase for 4 hours to reconvert the product to zeatin.

Figure 3:
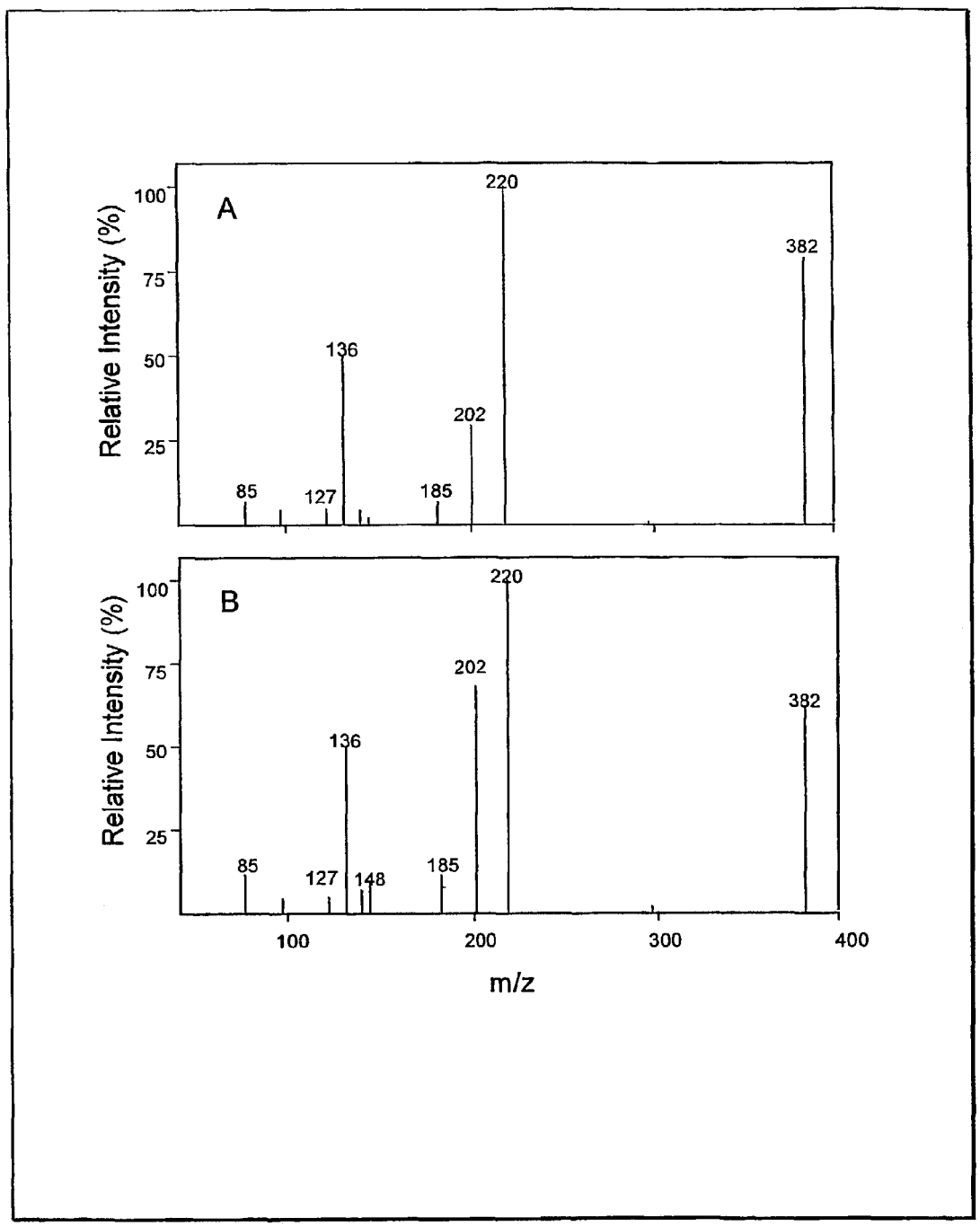

FIG. 3 shows respective mass spectrum profiles of reaction products with characteristic ion of cis-zeatin and the expected molecular mass of cis-zeatin O-glucoside (FIG. 3A), and standard of trans-zeatin O-glucoside (FIG. 3B).

FIG. 4 shows a comparison of nucleic acid residues 743–1133 of the open reading frame (ORF) from *Phaseolus lunatus* ZOG1 (SEQ ID NO: 1) and nucleic acid residues 764–1157 of the ORF from *Zea mays* cis-ZOG1 (SEQ ID NO: 7).

FIG. 5 shows a comparison of amino acid residues 14–459 of the open reading frame (ORF) from *Phaseolus lunatus* ZOG1 (SEQ ID NO: 2) and amino acid residues 9–467 of the ORF from *Zea mays* cis-ZOG1 (SEQ ID NO: 8).

SEQUENCE LISTINGS

The nucleic acid and amino acid sequences listed in the accompanying sequence listing are shown using standard letter abbreviations for nucleotide bases, and three-letter code for amino acids. Only one strand of each nucleic acid sequence is shown, but the complementary strand is understood to be included by any reference to the displayed strand.

SEQ ID NO: 1 shows the nucleic acid sequence of the *Phaseolus lunatus* zeatin O-glucosyltransferase (ZOG1) open reading frame (ORF).

SEQ ID NO: 2 shows the amino acid sequence of the *Phaseolus lunatus* zeatin O-glucosyltransferase (ZOG1) open reading frame (ORF).

SEQ ID NO: 3 shows the nucleic acid sequence of *Zea mays* EST-cdmah36.

SEQ ID NOS: 4 and 5 show the nucleic acid sequences of two polymerase chain reactions (PCR) primers used to amplify corn genomic DNA.

SEQ ID NO: 6 shows the nucleic acid sequence, designated as corn2, of the corn DNA fragment amplified by the PCR primers shown in SEQ ID NOS: 4 and 5.

SEQ ID NO: 7 shows the nucleic acid sequence of the ORF of cis-zeatin O-glucosyltransferase (cis-ZOG1) from *Zea mays*.

SEQ ID NO: 8 shows the deduced amino acid sequence of cis-ZOG1.

SEQ ID NOS: 9 and 10 show primers that can be used to amplify the ORF shown in SEQ ID NO: 7 to produce recombinant protein in pTRC 99A expression vector.

SEQ ID NO: 11 shows the cDNA sequence encoding cis-ZOG1.

DETAILED DESCRIPTION

I. Abbreviations and Explanations of Terms
A. Abbreviations

| | |
|---|---|
| $^{14}$C-cis-zeatin: cis-[8-$^{14}$C]zeatin | OXRZ: O-xylosylribosylzeatin |
| cis-Z: cis-zeatin | UDPG: uridine diphosphate glucose |
| Z: trans-zeatin | UDPX: uridine diphosphate xylose |
| OGZ: O-glucosylzeatin | ADPG: adenosine diphosphate glucose |
| OXZ: O-xylosylzeatin | TEA: triethylamine |
| DHZ: dihydrozeatin | ORF: open reading frame |
| OXDHZ: O-xylosyldihydrozeatin | MAb: monoclonal antibody |
| RZ: ribosylzeatin | EST: expressed sequence tag |
| ZOG: zeatin O-glucosyltransferase | |

B. Explanations of Terms

Unless otherwise noted, technical terms are used according to conventional usage. Definitions of common terms in molecular biology may be found in Lewin, *Genes VII*, Oxford University Press, 2000 (ISBN 0-19-879276-X); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: a Comprehensive Desk Reference*, VCH Publishers, Inc., 1995 (ISBN 1-56081-569-8). The nomenclature for DNA bases as set forth at 37 C.F.R § 1.822 and the standard three-letter codes for amino acid residues are used herein.

Figure 1:
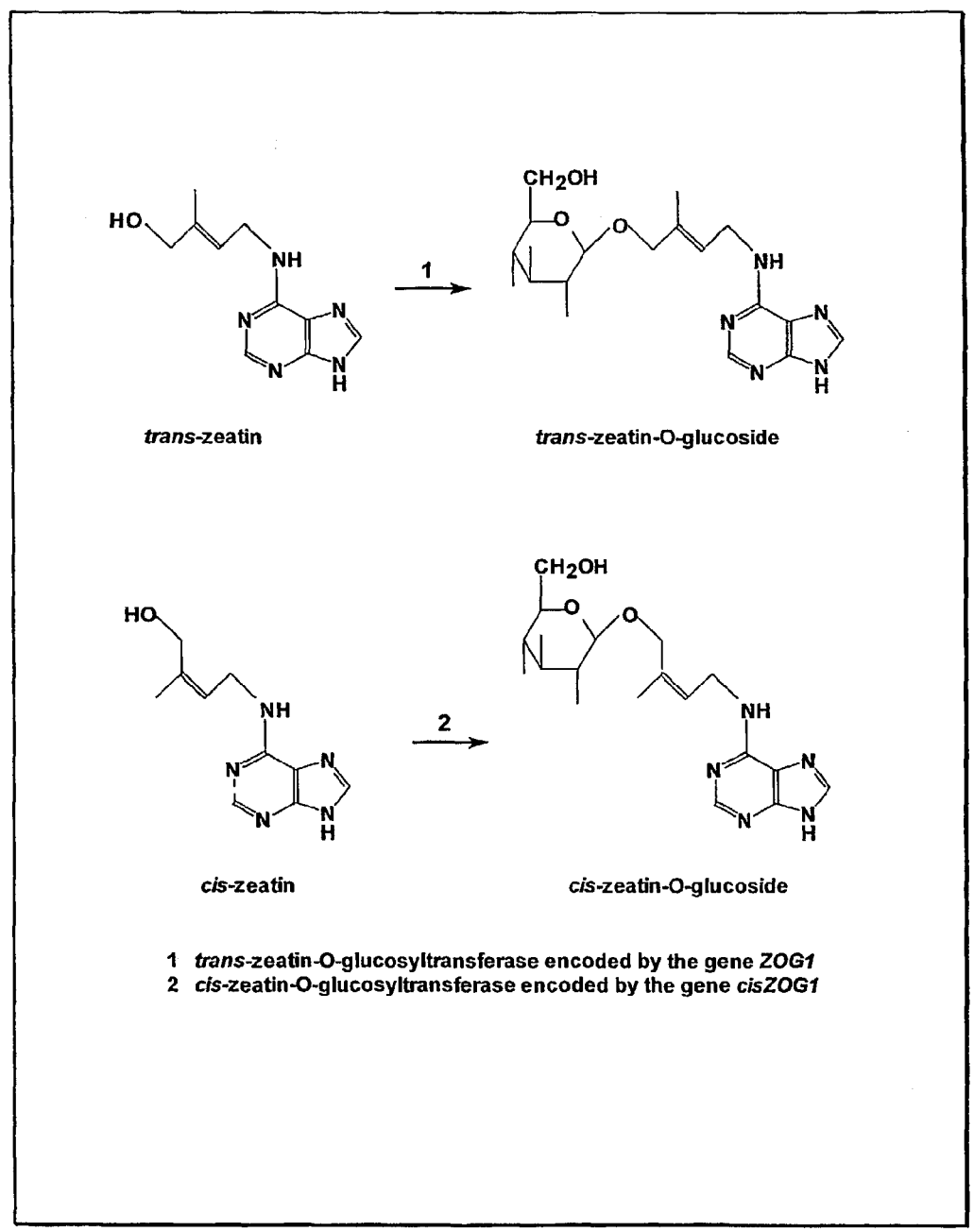
FIG. 1 shows the formation of trans-zeatin-O-glucoside and the formation of cis-zeatin-O-glucoside.

In order to facilitate review of the various embodiments, the following explanations of terms are provided:

cis-zeatin O-glucosyltransferase (cis-ZOG1): The defining functional characteristic of the cis-ZOG 1 enzyme is its ability to glucosylate cytokinins, such as cis-zeatin, and produce a product that is an O-glucoside of cytokinln. By way of example, the *Zea mays* cis-ZOG1 is capable of glucosylating cis-zeatin to form cis-O-glucosylzeatin, a conversion that is depicted in FIG. 1. This is in contrast to the trans-ZOG 1 isolated from Phaseolus lunatus which glycosylates trans-zeatin. The cis-ZOG1 activity can be measured using an assay similar to that described by Dixon et al. (Dixon et al., *Plant Physiol*. 90:1316–1321, 1989), described in detail below. This disclosure provides a cDNA and a gene encoding the cis-ZOG1 enzyme from *Zea mays*. However, the disclosure is not limited to this particular cis-ZOG1: other nucleotide sequences that encode cis-ZOG1 enzymes are also encompassed by the disclosure, including variants of the disclosed *Zea mays* cDNA and orthologous sequences from other plant species, the cloning of which is now enabled. Such sequences share the essential functional characteristic of encoding an enzyme that is capable of glucosylating cytokinins. Nucleic acid sequences that encode cis-zeatin O-glucosyltransferases and the proteins encoded by such nucleic acids share not only this functional characteristic, but also a specified level of sequence similarity (or sequence identity), as addressed below. The concept of sequence identity also can be expressed in the ability of two sequences to hybridize to each other under stringent conditions.

Isolated: An "isolated" biological component (such as a nucleic acid or protein or organeue) is a component that has been substantially separated or purified away from other biological components in the cell of the organism in which the component naturally occurs, i.e., other chromosomal and extra-chromosomal DNA, RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids.

Operably linked: A first nucleic acid sequence is "operably linked" with a second nucleic acid sequence whenever the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Ortholog: Two nucleotide or amino acid sequences are orthologs of each other if they share a common ancestral sequence and diverged when a species carrying that ancestral sequence split into two species. Orthologous sequences are also homologous sequences.

Probes and primers: Nucleic acid probes and primers may be readily prepared based on, the nucleic acid sequences provided. A "probe" comprises an isolated nucleic acid sequence attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al. (eds.), *Molecular Cloning: A Laboratory Manual*, 2nd ed., vol. 1–3, Cold Spring Harbor Laboratory Press, Cold Spring Harbor, N.Y., 1989; and Ausubel et al. (eds.) *Current Protocols in Molecular Biology*, Greene Publishing and Wiley-Interscience, New York (with periodic updates), 1987.

"Primers" are short nucleic acids, preferably DNA oligonucleotides 15 nucleotides or more in length, that are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

As noted, probes and primers are preferably 15 nucleotides or more in length; to enhance specificity, probes and primers of 20 or more nucleotides may be preferred.

Methods for preparing and using probes and primers are described, for example, in Sambrook et al. (eds.), *Molecular Cloning: A Laboratory Manual*, 2nd ed., vol. 1–3, Cold Spring Harbor Laboratory Press, Cold Spring Harbor, N.Y., 1989; Ausubel et al. (eds.), *Current Protocols in Molecular Biology*, Greene Publishing and Wiley-Interscience, New York (with periodic updates), 1987; and Innis et al., *PCR Protocols: A Guide to Methods and Applications*, Academic Press: San Diego, 1990. PCR primer pairs can be derived from a known sequence, for example, by using computer programs intended for that purpose such as Primer™ (Version 0.5, 1991, Whitehead Institute for Biomedical Research, Cambridge, Mass.). One of skill in the art will appreciate that the specificity of a particular probe or primer increases with the length of the probe or primer. For example, a primer comprising 20 consecutive nucleotides will anneal to a target with a higher specificity than a corresponding primer of only 15 nucleotides. Thus, in order to obtain greater specificity, probes and primers may be selected that comprise, by way of example, 10, 20, 25, 30, 35, 40, 50 or more consecutive nucleotides.

Purified: The term "purified" does not require absolute purity; rather, it is intended as a relative term. Thus, for example, a purified cis-ZOG1 preparation is one in which the cis-ZOG1 is more enriched than the protein in its natural environment within a cell. Preferably, a preparation of cis-ZOG1 is purified such that the cis-ZOG1 represents at least 50% of the total protein content of the preparation.

Recombinant: A "recombinant" nucleic acid is one having a sequence that is not naturally occurring or has a sequence made by an artificial combination of two otherwise-separated, shorter sequences. This artificial combination is often accomplished by chemical synthesis or, more commonly, by the artificial manipulation of isolated segments of nucleic acids, e.g. by genetic engineering techniques.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences are.

Methods for aligning sequences for comparison purposes are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene* 73:237–244, 1988; Higgins & Sharp, CABIOS 5:151–153, 1989; Corpet et al., *Nucleic Acids Research* 16:10881–10890, 1988; Huang, et al., *Computer Applications in the Biosciences* 8:155–165, 1992; and Pearson et al., *Methods in Molecular Biology* 24:307–331, 1994. Altschul et al., *J. Mol. Biol.*, 215:403–410, 1990, presents a detailed consideration of sequence alignment methods and homology calculations.

The NCBI Basic Local Alignment Search Tool (BLAST™, Altschul et al. *J. Mol. Biol.*, 215:403–410, 1990) is available from several sources, including the National Center for Biotechnology Information (NCBI, Bethesda, Md.) and on the Internet, for use in connection with the sequence-analysis programs blastp, blastn, blastx, tblastn and tblastx.

For comparisons of amino acid sequences of greater than about 30 amino acids, the "Blast 2 sequences" function in the BLAST™ program is employed using the default BLOSUM62 matrix set to default parameters, (gap existence cost of 11, and a per-residue gap cost of 1). When aligning short peptides (fewer than about 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 45%, at least 50%, at least 60%, at least 70%, at least 75%, at least 80%, at least 85%, at least 90%, or at least 95% sequence identity.

Specific Binding Agent: A "specific binding agent" is an agent that is capable of specifically binding to the cis-ZOG1, and may include polyclonal antibodies, monoclonal antibodies (including humanized monoclonal antibodies) and fragments of monoclonal antibodies such as Fab, F(ab')2 and Fv fragments, as well as any other agent capable of specifically binding to the epitopes on the proteins.

Substantial similarity: A first nucleic acid is "substantially similar" to a second nucleic acid if, when optimally aligned (with appropriate nucleotide insertions or deletions) with the other nucleic acid (or its complementary strand), there is nucleotide sequence identity in at least about 60%, 75%, 80%, 85%, 90% or 95% of the nucleotide bases. Sequence similarity can be determined by comparing the nucleotide sequences of two nucleic acids using the BLAST™ sequence analysis software (blastn) available from The National Center for Biotechnology Information. Such comparisons may be made using the software set to default settings (expect=10, filter=default, descriptions=500 pairwise, alignments=500, alignment view=standard, gap existence cost=11, per residue existence=1, per residue gap cost=0.85). Similarly, a first polypeptide is substantially similar to a second polypeptide if they show sequence identity of at least about 60%, 65%, 70%, 75%, 80%, 85%, 90%, or 95% or greater when optically aligned and compared using BLAST™ software (blastp) using default settings.

Transformed: A "transformed" cell is a cell into which a nucleic acid molecule has been introduced by molecular biology techniques. As used herein, the term "transformation" encompasses all techniques by which a nucleic acid molecule might be introduced into such a cell, including transfection with a viral vector, transformation with a plasmid vector, and introduction of naked DNA by electroporation, lipofection, and particle gun acceleration.

Transgenic plant: The term "transgenic plant," as used herein, refers to a plant that contains recombinant genetic material not normally found in plants of this type and that has been introduced into the plant in question (or into progenitors of the plant) by human manipulation. Thus, a plant that is grown from a plant cell into which recombinant DNA is introduced by transformation is a transgenic plant, as are all offspring of the transgenic plant that contain the introduced DNA (whether produced sexually or asexually).

Vector: A "vector" is a nucleic acid molecule as introduced into a host cell, thereby producing a transformed host cell. A vector may include nucleic acid sequences, such as an origin of replication, that permit the vector to replicate in a host cell. A vector may also include one or more selectable marker genes and other genetic elements known in the art.

II. Isolation of cDNA and Genomic Sequences Encoding cis-Zeatin O-glucosyltransferase from *Zea mays*

A. Overview of Experimental Procedures

The sequence of ZOG1 (zeatin O-glucosyltransferase) from *Phaseolus lunatus* (SEQ ID NO: 1) was compared with sequences contained in an EST database maintained by Pioneer Hi-Bred International Inc. (PHI). Candidate ESTs were further analyzed. Specific PCR primers were designed to bind to regions of conserved sequences found by comparing the glucosyltransferase, ZOG1, and a selected corn EST, cdmah36. These primers were then used to amplify corn genomic DNA to obtain a probe, CORN2 (SEQ ID NO: 6). The CORN2 probe was then used to screen cDNA libraries. This screen led to the identification of the cis-ZOG1 encoding sequence (SEQ ID NO: 11).

B. Methods

1. Construction of cDNA library from corn kernels. Total RNA was isolated from 35 DAP *Zea mays* kernels (inbred B73) using TriPure® reagent following the manufacturer's protocols (Boehringer Mannheim, Germany). mRNA was then isolated using the Poly A Ttract System III, according to the manufacturer's instructions (Promega, Madison, Wis.). The expression/cloning library was constructed using the SuperScript™ Plasmid System for cDNA Synthesis and Plasmid Cloning (Life Technologies, Inc., Rockville, Md.). First-strand synthesis was primed with a NotI-oligo-d(T) primer-adapter. Following second-strand synthesis SalI adapters were ligated to the cDNA, which was subsequently digested with NotI and size-fractionated. cDNA was directional inserted into a pSPORT1™ (Life Technologies, Inc., Rockville, Md.) plasmid following the manufacturer's procedure.

2. Selection of cDNA. The cDNA library was screen with a $^{32}$P-labeled insert of CORN2 using standard hybridization protocols.

3. Isolation of Recombinant Proteins. To obtain recombinant proteins, the ORF of the selected cDNA was amplified by PCR using primers (SEQ ID NOS: 9 and 10) that generated products having an NcoI site at the 5' and a XbaI site at the 3' terminus. The PCR products were digested with NcoI and XbaI restriction enzymes and ligated into a p Trc 99A expression vector (Pharmacia) modified to contain seven histidine residues (CAT or CAC), and transformed into the XL1 Blue cell line. Colonies were selected on AMP-LB plates. An individual colony was grown overnight in SOC-AMP media (F. M. Ausubel et al., Short Protocols in Molecular Biology, John Wiley and sons, 1989) and 0.5 mL of the culture was used to inoculate 50 mL of SOC-AMP media Induction was achieved with isopropyl-D-thiogalactoside (IPTG; 0.5 mL of 0.5 M) after cells were allowed to grow for 3–4 hours (OD at 595 nm of 0.8–1.0). After 4 hours cells were collected and frozen at −80 C overnight. Cells were resuspended in 0.5 mL of 0.2 M Tris pH 7.5 containing 1 mg/mL of lysozyme. Samples were incubated on ice for 30 minutes, frozen for 10 minutes at −80 C, thawed in cold water, and then DNAase (1 µg/10 µl supernatant) was added. After 10 minutes at room temperature, the samples were sonicated with four 15-second bursts to release proteins from cells. Soluble proteins were collected after centrifugation and used for enzyme assays.

4. Enzyme assays and analysis of reaction products. Enzyme activity was determined as reported previously (Dixon et al., *Plant Physiol*. 90:1316–1321, 1989). Briefly, a specified amount of recombinant protein, $^{14}$C-labeled cis-zeatin (specific activity of 24 mCi/mmol), and a glycosyl donor (4 mM of UDPG) were incubated in $MgCl_2$ (0.07 M) in 0.17 M Tris, pH 8.0. Reaction products were then analyzed by HPLC (Dixon et al., *Plant Physiol*. 90:1316–1321, 1989).

5. Isolation of Genomic Sequence of cis-Zeatin O-glucosyltransferase (cis-ZOG1) from *Zea mays*. Isolation of the genomic sequence was based on the principles of PCR (Ochman et al., PCR Technology-Principles and Applications for DNA Amplification 105–111, 1989). DNA was isolated from *Zea mays* using a modified CTAB (hexadecyltrimethylammonium bromide) method (Doyle et al., *Focus* 12:13–15, 1990). PCR was performed with primers homologous to the 5' and 3' regions of the cDNA clone. To obtain genomic sequence inclusive of the expressed region (cDNA), standard PCR reactions were performed using pairs of primers based on the sequence of the cDNA. The products obtained from PCR were analyzed on a 1% Sea Plaque gel. Bands of interest were excised and DNA was purified with Qiaex II™ Gel Extraction Kit (Qiagen, Santa Clarita, Calif.). The products were ligated into a pGem-T vector (Promega, Madison, Wis.) for sequencing.

C. Results

1. Identification of candidate EST, design of PCR primers and synthesis of a specific probe. The sequence of ZOG1 (zeatin O-glucosyltransferase) from *Phaseolus lunatus* (SEQ ID NO: 1) was compared with sequences contained in the EST database of Pioneer Hi-Bred International Inc. (PHB). The partial sequence of an EST, cdmah36 (SEQ ID NO: 3) was judged to have the highest homology. Based on the sequence of ZOG1 and EST-cdmah36, a set of PCR primers was designed (SEQ ID NOS: 4 and 5) to amplify corn genomic DNA to generate a 292-bp probe designated as CORN2 (SEQ ID NO: 6).

2. Isolation of the cDNA and the gene. A cDNA library (P0033) from PHB constructed from 35-DAP (day after pollination) corn kernels of the inbred B73 was probed with CORN2, and a cDNA containing an ORF of 1401 bp encoding a protein of 51.1 kD (SEQ ID NOS: 7 and 8, respectively) was isolated. The corresponding genomic sequence was obtained by PCR using primers based on the flanking sequence of the ORF to ampl genomic DNA of B73. The isolated gene did not contain any introns.

3. Enzyme activity of the gene product. To determine the biological activity and function of the peptide encoded by the selected cDNA, the ORF was amplified using the primers (SEQ ID NOS: 9 and 10), digested with the restriction enzymes NcoI and XbaI and spliced into the PHT plasmid. Recombinant protein was obtained using protocols previously described (Martin et al., *Proc. Natl. Acad. Sci. USA* 96:284–289, 1999a; Martin et al., *Plant Physiol.* 120:553–557, 1999). The function of the recombinant protein was determined. The protein is a cytokinin metabolic enzyme mediating the formation of O-glucosyl-cis-zeatin from cis-zeatin and UDPG (FIG. 2B). The authenticity of the reaction product (cis-zeatin O-glucoside) was demonstrated by the re-conversion of the reaction product to cis-zeatin by β-glucosidase (FIG. 2C), and by the MS profile of the product (FIG. 3), exhibiting the characteristic spectrum of cis-zeatin but with the expected molecular mass of its O-glucoside. The enzyme does not use trans-zeatin, trans-ribosylzeatin, dihydrozeatin or ribosyldihydrozeatin as the substrate.

The gene is designated as cis-ZOG1 and is deemed new based on BLAST™ searches of public databases. The only genes with significant homology are ZOG1 and ZOX1 of Phaseolus. The enzyme encoded by cis-ZOG1, and the function of the enzyme are novel and have not been described previously.

4. Homology to Phaseolus zeatin O-glycosyltransferases ZOG1 and ZOX1. The DNA of cis-ZOG1 is 60% identical to ZOG1 (FIG. 4). However, the longest contiguous segment is only 14 bp. The amino acid sequence is 41% identical to ZOG1 with a longest identical stretch of amino acids being ten residues (FIG. 5). The amino acid sequence identity to ZOX1 is also 41% (not shown because ZOG1 and ZOX1 have 93% and 87% identical DNA and amino acid sequences).

The following examples are illustrative of various embodiments.

EXAMPLE ONE

Preferred Method for Producing cis-ZOG1 Nucleic acids

With the provision herein of the cis-ZOG1 ORF, the polymerase chain reaction (PCR) may now be utilized in a preferred method for producing nucleic acid sequences encoding cis-ZOG1 ORF. PCR amplification of the disclosed *Zea mays* sequences may be accomplished either by direct PCR from a plant cDNA library or by Reverse-Transcription PCR (RT-PCR) using RNA extracted from plant cells as a template. Methods and conditions for both direct PCR and RT-PCR are known in the art and are described in Innis et al. (Innis et al., *PCR Protocols, A Guide to Methods and Applications*, Academic Press Inc., 1990). Suitable plant cDNA libraries for direct PCR include the Arabidopsis cDNA library described by Newman et al. (Newman et al., *Plant Physiol.* 106:1241–1255, 1994) and *Zea mays* cDNA libraries constructed as described above.

The selection of PCR primers is made according to the portions of the cDNA or gene that are to be amplified. Primers may be chosen to amplify small segments of the cDNA, the open reading frame, the entire cDNA molecule or the entire gene sequence. Variations in amplification conditions may be required to accommodate primers of differing lengths; such considerations are well known in the art and are discussed in Innis et al. (Innis et al., *PCR Protocols, A Guide to Methods and Applications*, Academic Press, Inc., 1990), Sambrook et al. (Sambrook et al., *Molecular Cloning: A Laboratory Manual*, Cold Spring Harbor Press, 1989), and Ausubel et al. (Ausubel et al., *Current Protocols in Molecular Biology*, Greene Publishing Associates and Wiley-Intersciences, 1987).

By way of example only, the entire cis-ZOG1 ORF as shown in SEQ ID NO: 7 may be amplified using the following combination of the primers shown in SEQ ID NOS: 9 and 10. These primers are illustrative only; it will be appreciated by one skilled in the art that many different primers may be derived from the provided ORF in order to amplify particular regions of this molecule. Resequencing of PCR products obtained by these amplification procedures is recommended to facilitate confirmation of the amplified sequence and also to provide information on natural variation on this sequence in different ecotypes and plant populations.

Oligonucleotides that are derived from the disclosed *Zea mays* sequences are encompassed within the scope of the present disclosure. Preferably, such oligonucleotide primers will comprise a sequence of at least 15–20 consecutive nucleotides of the disclosed *Zea mays* sequence. To enhance amplification specificity, oligonucleotide primers comprising at least 15, 20, 25, 30, 35, 40, 45 or 50 consecutive nucleotides of these sequences may also be used.

EXAMPLE TWO

Isolation of Homologous Gene Sequence from other Plant Species

With the provision herein of the disclosed *Zea mays* sequence, the cloning of orthologous cDNAs and genes from other plant species by standard methodologies is now enabled. Thus, the present disclosure includes methods of isolating both cDNA and genomic sequences encoding cis-ZOG1. Both conventional hybridization and PCR amplification procedures may be utilized to clone such sequences. Common to both of these techniques is the hybridization of probes or primers derived from the disclosed *Zea mays* sequences to a target nucleotide preparation, which may be, in the case of conventional hybridization approaches, a cDNA or genomic library or, in the case of PCR amplification, a cDNA or genomic library, or an mRNA preparation.

Direct PCR amplification may be performed on cDNA or genomic libraries prepared from the plant species in question, or RT-PCR may be performed using mRNA extracted from the plant cells using standard methods. PCR primers will comprise at least 15 consecutive nucleotides of the disclosed *Zea mays* sequence. One of skill in the art will appreciate that sequence differences between the disclosed *Zea mays* sequence and the target nucleic acid to be amplified may result in lower amplification efficiencies. To compensate for this, PCR primers from a different region of the target sequence may be used. Where lower annealing temperatures are used, sequential rounds of amplification using nested primer pairs may be necessary to enhance specificity.

For conventional hybridization techniques (described further in Example Four below) the hybridization probe is preferably conjugated with a detectable label such as a radioactive label, and the probe is preferably at least 20 nucleotides in length. As is well known in the art, increasing the length of hybridization probes tends to give enhanced specificity. The labeled probe derived from the *Zea mays* cDNA or ORF sequence may be hybridized to a plant cDNA or genomic library, and the hybridization signal may be detected using means known in the art. The hybridizing colony or plaque (depending on the type of library used) is then purified, and the cloned sequence contained in that colony or plaque is isolated and characterized.

Homologs of the *Zea mays* cis-ZOG1 alternatively may be obtained by immunoscreening of an expression library. With the provision herein of the disclosed *Zea mays* nucleic acid sequence, the enzymes may be expressed and purified in a heterologous expression system (e.g. *E. coli*) and used to raise antibodies (monoclonal or polyclonal) specific for the cis-ZOG1 protein. Antibodies also may be raised against synthetic peptides derived from the *Zea mays* amino acid sequences presented herein. Methods of raising antibodies are well known in the art and are described in Harlow and Lane (Harlow et al., *Antibodies, A Laboratory Manual*, Cold Spring Harbor Laboratory, New York, 1988). Such antibodies then can be used to screen an expression cDNA library produced from the plant from which it is desired to clone the cis-ZOG1 gene ortholog, using the methods described above. The selected cDNAs can be confirmed by sequencing and enzyme activity.

The disclosed *Zea mays* sequences, and homologs of these sequences from other plants, may be incorporated into transformation vectors and introduced into plants to modify cis-ZOG1 activity in such plants, as described in Example Three below. It is anticipated that the native cis-ZOG1 gene promoter may be useful particularly in the practice of the present disclosure in that the promoter may be used to drive the expression of cis-ZOG1 transgenes, such as antisense constructs. For example, by using the native cis-ZOG1 gene promoter, expression of these transgenes may be regulated in coordination with the native cis-ZOG1 gene (for example, in the same temporal or tissue-specific expression patterns).

EXAMPLE THREE

Transgenic Plants with Modified cis-ZOG1 Expression

Once a gene (or cDNA) encoding a protein involved in the determination of a particular plant characteristic has been isolated, standard techniques may be used to express the cDNA in transgenic plants in order to modify that particular plant characteristic. The basic approach is to clone the cDNA into a transformation vector, such that the cDNA is operably linked to control sequences (e.g., a promoter) that direct expression of the cDNA in plant cells. The transformation vector is then introduced into plant cells by one of a number of techniques (e.g., electroporation, Agrobacteria infection and biolistic delivery), and progeny plants containing the introduced cDNA are selected. Preferably all or part of the transformation vector will stably integrate into the genome of the plant cell. That part of the transformation vector that integrates into the plant cell and that contains the introduced cDNA and associated sequences for controlling expression (i.e., the introduced "transgene") may be referred to as the recombinant expression cassette.

Selection of progeny plants containing the introduced transgene may be made based upon the detection of an altered phenotype. Such a phenotype may result directly from the cDNA cloned into the transformation vector or may be manifested as enhanced resistance to a chemical agent (such as an antibiotic) as a result of the inclusion of a dominant selectable marker gene incorporated into the transformation vector.

The choice of (a) control sequences and (b) how the cDNA (or selected portions of the cDNA) are arranged in the transformation vector relative to the control sequences determine, in part, how the plant characteristic affected by the introduced cDNA is modified. For example, the control sequences may be tissue specific, in which instances the cDNA is expressed only in particular tissues of the plant (e.g., pollen, seed) and the affected characteristic is modified only in those tissues. The cDNA sequence may be arranged relative to the control sequence such that the cDNA transcript is expressed normally, or in an antisense orientation. Expression of an antisense RNA corresponding to the cloned cDNA will result in a reduction of the targeted gene product (the targeted gene product being the protein encoded by the plant gene from which the introduced cDNA was derived). Over-expression of the introduced cDNA, resulting from a plus-sense orientation of the cDNA relative to the control sequences in the vector, may lead to an increase in the level of the gene product, or may result in co-suppression (also termed "sense suppression") of that gene product.

Successful examples of the modification of plant characteristics by transformation with cloned cDNA sequences are replete in the technical and scientific literature. Selected examples, that serve to illustrate the current knowledge in this field of technology, and which are herein incorporated by reference, include:

U.S. Pat. No. 5,451,514 to Boudet (modification of lignin synthesis using antisense RNA and co-suppression);

U.S. Pat. No. 5,443,974 to Hitz (modification of saturated and unsaturated fatty acid levels using antisense RNA and co-suppression);

U.S. Pat. No. 5,530,192 to Murase (modification of amino acid and fatty acid composition using antisense RNA);

U.S. Pat. No. 5,455,167 to Voelker (modification of medium chain fatty acids)

U.S. Pat. No. 5,231,020 to Jorgensen (modification of flavenoids using co-suppression);

U.S. Pat. No. 5,583,021 to Dougherty (modification of virus resistance by expression of plus-sense untranslatable RNA);

WO 96/13582 (modification of seed VLCFA composition using over expression, co-suppression and antisense RNA in conjunction with the Arabidopsis FAE1 gene); and WO 95/15387 (modification of seed VLCFA composition using over expression of jojoba wax synthesis gene).

These examples include descriptions of transformation-vector selection, transformation techniques, and the construction of constructs designed to over-express the introduced cDNA or to express antisense RNA corresponding to the cDNA. In light of the foregoing and the disclosed *Zea mays* sequences, it is apparent that one of skill in the art will be able to introduce these nucleic acids, or homologous or derivative forms of these molecules (e.g., antisense forms), into plants in order to produce plants having modified cis-zeatin O-glucosyltransferase activity. Modification of the activity of cis-ZOB1 in plants will permit controlled modification of not only zeatin function, but also other cytokinins and, as a consequence of the interdependent regulation of plant hormones, other hormones. The result can be altered plant development with agricultural and economic consequences.

a. Plant Types

Zeatins are found in all plant types. Thus, DNA molecules (e.g., the cis-ZOG1 cDNA and homologs of this sequence and derivatives such as antisense forms) may be introduced into any plant type in order to modify the cis-ZOG1 activity in the plant. The sequences of the present disclosure may be used to modify cis-zeatin O-glucosyltransferase activity in any higher plant, including monocotyledonous, dicotyledenous, and gymnosperm plants, including, but not limited to *Zea mays*, wheat, rice, barley, soybean, beans in general, rape/canola, alfalfa, flax, sunflower, safflower, brassica, pine trees such as loblolly pine and Douglas fir, cotton, flax, peanut, clover, vegetables such as lettuce, tomato, cucurbits, potato, carrot, radish, pea, lentils, cabbage, broccoli, brussel sprouts, peppers; tree fruits such as apples, pears, peaches, apricots; flowers such as carnations and roses.

b. Vector Construction, Choice of Promoters

A number of recombinant vectors suitable for stable transfection of plant cells or for the establishment of transgenic planes have been described including those described in Pouwels et al., (Pouwels et al., *Cloning Vectors: A Laboratory Manual*, 1987), Weissbach and Weissbach, (Weissbach et al., *Methods for Plant Molecular Biology*, Academic Press, 1989), and Gelvin et al., (Gelvin et al., *Plant Molecular Biology Manual*, Kluwer Academic Publishers, 1990). Typically, plant-transformation vectors include one or more cloned plant genes (or cDNAs) under the transcriptional control of 5' and 3' regulatory sequences and a dominant selectable marker. Such plant-transformation vectors typically also contain a promoter-regulatory region (e.g., a regulatory region controlling inducible or constitutive, environmentally-or developmentally-regulated, or cell- or tissue-specific expression), a transcription-initiation start site, a ribosome-binding site, an RNA-processing signal, a transcription-termination site, and/or a polyadenylation signal.

Examples of constitutive plant promoters that may be useful for expressing the cDNA include: the cauliflower mosaic virus (CaMV) 35S promoter, which confers constitutive, high-level expression in most plant tissues (see, e.g., Odel et al., *Nature* 313:810, 1985; Dekeyser et al., *Plant Cell* 2:591, 1990; Terada at al., *Mol. Gen. Genet.* 220:389, 1990; Benfey et al., *Science* 250:959–966, 1990); the nopaline synthase promoter (An et al., *Plant Physiol.* 88:547, 1988); and the octopine synthase promoter (Fromm et al., *Plant Cell* 1:977, 1989).

A variety of plant-gene promoters that are regulated in response to environmental, hormonal, chemical, and/or developmental signals, also can be used for expression of the cDNA in plant cells. These include promoters regulated by: (a) heat (Callis et al., *Plant Physiol.* 88:965, 1988; Ainley et al., *Plant Mot. Biol.* 22:13–23, 1993; Gilmartin et al., *The Plant Cell* 4:839–949, 1992); (b) light (e.g., the pea rbcS-3A promoter, Kuhlemeier et al., *Plant Cell* 1:471, 1989, and the *Zea mays* rbcS promoter, Schaffner et al., *Plant Cell* 3:997, 1991); (c) hormones, such as abscisic acid (Marcotte et al., *Plant Cell* 1:969, 1989); (d) wounding (e.g., wunI, Siebertz et al., *Plant Cell* 1:961, 1989); and (e) chemicals such as methyl jasminate or salicylic acid (see also Gatz et al., *Ann Rev. Plant Physiol. Plant Mol. Biol.* 48:89–108, 1997) also can be used to regulate gene expression.

Alternatively, tissue specific (root, leaf, flower, and seed, for example) promoters (Carpenter et al., *The Plant Cell* 4:557–571, 1992; Denis et al., *Plant Physiol.* 101:1295–1304, 1993; Opperman et al., *Science* 263:221–223, 1993; Stockhause et al., *The Plant Cell* 9:479–489, 1997; Roshal et al., *EMBO J.* 6:1155, 1987; Schernthaner et al., *EMBO J.* 7:1249, 1988; and Bustos et al., *Plant Cell* 1:839, 1989) can be fused to the coding sequence to obtain particular expression in respective organs. In addition, the timing of the expression can be controlled by using promoters such as those acting at senescence (Gan et al., *Science* 270:1936–1988, 1995) or late seed development (Odell et al., *Plant Physiol.* 106: 447–458, 1994).

Plant-transformation vectors also may include RNA processing signals, for example, introns, that may be positioned upstream or downstream of the ORF sequence in the transgene. In addition, the expression vectors also may include additional regulatory sequences from the 3'-untranslated region of plant genes, e.g., a 3'-terminator region to increase mRNA stability of the mRNA, such as the PI-II terminator region of potato or the octopine or nopaline synthase 3'-terminator regions.

Finally, as noted above, plant-transformation vectors also may include dominant selectable marker genes to allow for the ready selection of transformants. Such genes include those encoding antibiotic-resistance genes (e.g., resistance to hygromycin, kanamycin, bleomycin, G418, streptomycin, or spectinomycin) and herbicide-resistance genes (e.g. phosphinothricin acetyltransferase).

c. Arrangement of cis-ZOG1 Sequence in Vector

The particular arrangement of the cis-zeatin O-glucosyltransferase sequence in the transformation vector will be selected according to the type of expression of the sequence that is desired.

Where enhanced cis-zeatin O-glucosyltransferase activity is desired in the plant, the cis-zeatin O-glucosyltransferase can be ligated to a constitutive high-level promoter such as the CaMV 35S promoter. As noted below, modification of cis-zeatin O-glucosyltransferase synthesis also may be achieved by introducing into a plant a transformation vector containing a variant form of the disclosed *Zea mays* sequences. For example, a form can vary from the exact nucleotide sequence of the cis-zeatin O-glucosyltransferase ORF (SEQ ID NO: 7), but still encode a protein that retains the functional characteristic of the cis-zeatin O-glucosyltransferase protein, i.e., O-glucosylation of cytokinins, such as cis-zeatin.

In contrast, a reduction of cis-zeatin O-glucosyltransferase activity in the transgenic plant may be obtained in a number of different ways. For example, a reduction in protein product can be achieved through the use of antisense sequences, ribozymes, co-suppression, untranslatable RNAs, and/or dominant negative mutants.

For antisense suppression, the disclosed *Zea mays* sequences are arranged in reverse orientation relative to the promoter sequence in the transformation vector. The introduced sequence need not be the full-length version of the disclosed *Zea mays* sequence, and need not be exactly homologous to the endogenous cis-zeatin O-glucosyltransferase found in the plant type to be transformed. Generally, however, where the introduced sequence is of shorter length, a higher degree of homology to the endogenous zeatin O-glucosyltransferase sequence will be needed for effective antisense suppression. Preferably, the introduced antisense sequence in the vector will be at least 30 nucleotides in length, and improved antisense suppression will typically be observed as the length of the antisense sequence increases. Preferably, the length of the antisense sequence in the vector will be greater than 100 nucleotides. Transcription of an antisense construct as described results in the production of RNA molecules that are the reverse complement of mRNA molecules transcribed from the endogenous cis-zeatin O-glucosyltransferase gene in the plant cell. Although the exact mechanism by which antisense RNA molecules interfere with gene expression has not been elucidated, it is believed that antisense RNA molecules bind to the endogenous mRNA molecules and thereby inhibit translation of the endogenous mRNA.

Suppression of endogenous cis-ZOG1 expression also can be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haseloff. The inclusion of ribozyme sequences within antisense RNAs may be used to confer RNA-cleaving activity on the antisense RNA, such that endogenous mRNA molecules that bind to the antisense RNA are cleaved, which in turn leads to an enhanced antisense inhibition of endogenous gene expression.

Constructs in which the disclosed *Zea mays* sequences (or variants thereof) are overexpressed may also be used to obtain co-suppression of the endogenous cis-ZOG1 in the manner described in U.S. Pat. No. 5,231,021 to Jorgensen. Such co-suppression (also termed "sense suppression") does not require that the entire disclosed *Zea mays* sequence be introduced into the plant cells, nor does it require that the introduced sequence be exactly identical to the endogenous cis-ZOG1 sequence. However, as with antisense suppression, the suppressive efficiency will be enhanced as: (1) the introduced sequence is lengthened, and (2) the sequence similarity between the introduced sequence and the endogenous cis-ZOB1 gene is increased.

Constructs expressing an untranslatable form of the cis-ZOG1 mRNA also may be used to suppress the expression of endogenous cis-ZOG1. Methods for producing such constructs are described in U.S. Pat. No. 5,583,021 to Dougherty et al. Preferably, such constructs are made by introducing a premature stop codon into the cis-ZOG1 ORF.

Finally, dominant negative mutant forms of the disclosed *Zea mays* proteins may be used to block endogenous cis-ZOG1 activity. Such mutants require the production of mutated forms of the cis-ZOG1 protein that bind to zeatin but do not catalyze the enzymatic step.

d. Transformation and Regeneration Techniques

Transformation and regeneration of both monocotyledonous and dicotyledonous plant cells are now routine, and the selection of the most appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; transformation mediated by polyethylene glycol (PEG); transformation using viruses; micro-injection of plant cells; micro-projectile bombardment of plant cells; vacuum infiltration; and transformation mediated by *Agiobacterium tumefaciens* (AT). Typical procedures for transforming and regenerating plants are described in the patent documents listed at the beginning of this section.

e. Selection of Transformed Plants

Following transformation and regeneration of plants with the transformation vector, transformed plants are preferably selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described herein to determine whether cis-ZOG1 activity has been altered as a result of the introduced transgene. In addition, antisense or sense suppression of the endogenous cis-ZOG1 may be detected by analyzing mRNA expression on Northern blots.

EXAMPLE FOUR

Production of Sequence Variants

As noted above, modification of cis-zeatin O-glucosyltransferase activity in plant cells can be achieved by transforming plants with the disclosed *Zea mays* sequences, antisense constructs based on the disclosed *Zea mays* sequences, or other variants of the disclosed *Zea mays* sequences. With the provision of the disclosed *Zea mays* sequences herein, the creation of variants on these sequences by standard mutagenesis techniques is now enabled.

Variant DNA molecules include those created by standard DNA mutagenesis techniques, for example, M13 primer mutagenesis. Details of these techniques are provided in Ch. 15 of Sambrook et al. (Sambrook et al., *Molecular Cloning. A Laboratory Manual*, Spring Harbor, N.Y., 1989). By the use of such techniques, variants may be created that differ in minor ways from the disclosed *Zea mays* sequences. DNA molecules and nucleotide sequences that are derivatives of those specifically disclosed herein and that differ from those disclosed by the deletion, addition, or substitution of nucleotides while still encoding a protein that possesses the functional characteristic of the cis-zeatin O-glucosyltransferase protein (i.e., the ability to convert cis-zeatin to cis-O-glucosylzeatin) are comprehended by this disclosure. DNA molecules and nucleotide sequences that are derived from the disclosed *Zea mays* sequences include DNA sequences that hybridize under stringent conditions to the DNA sequences disclosed, or fragments thereof.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al. (Sambrook et al., *Molecular Cloning: A Laboratory Manual*, Spring Harbor, N.Y., 1989), chapters 9 and 11, herein incorporated by reference. By way of illustration only, a hybridization experiment may be performed by hybridization of a DNA molecule (for example, a variant of the *Zea mays* cis-zeatin O-glucosyltransferase ORF sequence) to a target DNA molecule (for example, the *Zea mays* cis-zeatin O-glucosyltransferase gene sequence) which has been electrophoresed in an agarose gel and transferred to a nitrocellulose membrane by Southern blotting (Southern, *J. Mol. Biol.* 98:503, 1975). This technique is well known in the art and described in Sambrook et al., *Molecular Cloning: A Laboratory Manual*, Spring Harbor, N.Y., 1989. Hybridization with a target probe labeled with $[^{32}P]$-dCTP is generally carried out in a solution of high ionic strength such as 6×SSC at a temperature that is 20–25° C. below the melting temperature, $T_m$, described below. For such Southern hybridization experiments where the target DNA molecule on the Southern blot contains 10 ng of DNA or more, hybridization typically is carried out for 6–8 hours using 1–2 ng/mL radiolabeled probe (of specific activity equal to $10^9$ CPM/μg or greater). Following hybridization, the nitrocellulose filter is washed to remove background hybridization. The washing conditions should be as stringent as possible to remove background hybridization while retaining a specific hybridization signal. The term $T_m$ represents the temperature above which, under the prevailing ionic conditions, the radiolabeled probe molecule will not hybridize to its target DNA molecule. The $T_m$ of such a hybrid molecule may be estimated from the following equation (Bolton et al., *Proc. Natl. Acad. Sci. USA* 48:1390, 1962):

$$T_m = 81.5_EC - 16.6(\log_{10}[Na^+]) + 0.41(\% \ G+C) - 0.63(\% \ \text{formamide}) - (600/l)$$

Wherein l=the length of the hybrid in base pairs. This equation is valid for concentrations of $Na^+$ in the range of 0.01 M to 0.4 M, but it is less accurate for calculations of $T_m$ in solutions of higher $[Na^+]$. The equation is also primarily valid for DNAs whose G+C content is in the range of 30% to 75%, and it applies to hybrids greater than 100 nucleotides in length (the behavior of oligonucleotide probes is described in detail in Ch. 11 of Sambrook et al., *Molecular Cloning: A Laboratory Manual*, Spring Harbor, N.Y., 1989).

Thus, by way of example, for a 150 base pair DNA probe derived from the first 150 base pairs of the open reading frame of the *Zea mays* cis-ZOG1 cDNA (with a hypothetical % GC=45%), a calculation of hybridization conditions required to give particular stringencies may be made as follows:

For this example, it is assumed that the filter will be washed in 0.3×SSC solution following hybridization, thereby $[Na^+]$=0.045M; % GC=45%; formamide concentration=0; l=150 base pairs; and $T_m$=81.5° C.−16($\log_{10}[Na^+]$)+(0.41×45)−(600/150)=74.4° C.

The $T_m$ of double-stranded DNA decreases by 1–1.5° C. with every 1% decrease in homology (Bonner et al., *J. Mol. Biol.* 81:123, 1973). Therefore, for this example, washing the filter in 0.3×SSC at 59.4–64.4° C. will produce a stringency of hybridization equivalent to 90%. Alternatively, washing the hybridized filter in 0.3×SSC at a temperature of 65.4–68.4° C. will yield a hybridization stringency of 94%. The above example is provided entirely by way of theoretical illustration. One skilled in the art will appreciate that other hybridization techniques may be utilized, and that variations in experimental conditions will necessitate alternative calculations for stringency.

DNA sequences from plants that encode a protein having cis-zeatin O-glucosyltransferase activity and that hybridize under hybridization conditions of at least 75%, more preferably at least 80%, more preferably at least 85%, more preferably at least 90% and most preferably at least 95% stringency are encompassed within the present disclosure.

The degeneracy of the genetic code further widens the scope of the present disclosure as the degeneracy enables major variations in the nucleotide sequence of a DNA molecule while maintaining the amino acid sequence of the encoded protein. For example, the second amino acid residue of the *Zea mays* cis-ZOG1 protein is alanine. This is encoded in the *Zea mays* cis-ZOG1 open reading frame by the nucleotide codon triplet GCG. Because of the degeneracy of the genetic code, three other nucleotide codon triplets-GCA, GCC and GCT-also code for alanine. Thus, the nucleotide sequence of the *Zea mays* cis-ZOG1 ORF could be changed at this position to any of these three codons without affecting the amino acid composition of the encoded protein or the characteristics of the protein. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences which encode a cis-ZOG1 protein but which vary from the disclosed nucleic acid sequences by virtue of the degeneracy of the genetic code.

One skilled in the art will recognize that DNA-mutagenesis techniques may be used not only to produce variant DNA molecules, but also facilitate the production of proteins that differ in certain structural aspects from the disclosed *Zea mays* proteins, such proteins being clearly derivative of the disclosed *Zea mays* proteins and retaining the essential functional characteristics of cis-ZOG1. Newly derived proteins also may be selected in order to obtain variations on the characteristics of the disclosed *Zea mays* proteins, as will be more fully described below. Such derivatives include those with variations in amino acid sequence including minor deletions, additions and substitutions, and protein fusions that contain a catalytically functional region of a cis-ZOG1 protein or sequence variant or ortholog thereof.

While the site for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues. Within a single substituted amino acid sequence, there may occur multiple substitutions, for instance two or more, 5 or more, 10 or more, 15 or more, 30 or more, or as many as 50 substitutions within a single polypeptide. In some embodiments, the number of amino acid substitutions is measured based on a percentage of the overall length of the resultant polypeptide, and thus it is contemplated that there may be about 0.5%, about 1%, about 3%, about 5%, about 7%, about 10%, about 15%, or more substitutions within a single polypeptide.

Insertions usually will be on the order of about from 1 to 10 amino acid residues; and deletions will range about from 1 to 30 residues. In some embodiments, longer insertions (such as fusions) and/or deletions are contemplated. Deletions or insertions may be made in adjacent pairs, i.e., a deletion of 2 residues or insertion of 2 residues, or multiples of pairs. Substitutions, deletions, insertions, or any combination thereof may be combined to arrive at a final construct. Obviously, the mutations that are made in the DNA encoding the protein should not place the sequence out of reading frame and usually will not create complementary regions that could produce secondary mRNA structure.

Also contemplated herein are variants of the provided proteins, which are fusion proteins. Fusion proteins contain relatively long lengths of additional amino acids, generally of greater than 10 amino acids in length, for instance at least 50, at least 100, at least 150, at least 200, at least 250, at least 500, at least 750, at least 1000, or more amino acids.

Substitutional variants are those in which at least one residue in the amino acid sequence has been removed and a different residue inserted in its place. Such substitutions generally are made in accordance with the following Table 1 when it is desired to finely modulate the characteristics of the protein. Table 1 shows amino acids that may be substituted for an original amino acid in a protein and that are regarded as conservative substitutions.

TABLE 1

Listing of Conservative Amino Acid Substitutions

| Original Residue | Conservative Substitutions |
|---|---|
| ala | ser |
| arg | lys |
| asn | gln; his |
| asp | glu |
| cys | ser |
| gln | asn |
| glu | asp |
| gly | pro |
| his | asn; gln |
| ile | leu, val |
| leu | ile; val |
| lys | arg; gln; glu |
| met | leu; ile |
| phe | met; leu; tyr |
| ser | thr |
| thr | ser |
| trp | tyr |
| tyr | trp; phe |
| val | ile; leu |

Substantial changes in enzymatic function or other features are made by selecting substitutions that are less conservative than those in Table 1, i.e., selecting residues that differ more significantly in their effect on maintaining: (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in protein properties will be those in which: (a) a hydrophilic residue, e.g. seryl or threonyl, is substituted for (or by) a hydrophobic residue, e.g., leucyl, isoleucyl, phenylalanyl, valyl, or alanyl; (b) a cysteine or proline is substituted for (or by) any other residue; (c) a residue having an electropositive side chain, e.g. lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the cis-ZOG1 protein by analyzing the ability of the derivative proteins to catalyze the conversion of cis-zeatin to cis-O-glucosylzeatin. These assays may conveniently be performed using the assay described above.

EXAMPLE FIVE

Production of Recombinant cis-ZOG1 Using Heterologous Expression Systems

Many different expression systems are available for expressing cloned nucleic acid molecules. Examples of prokaryotic and eukaryotic expression systems that are routinely used in laboratories are described in Chapters 16–17 of Sambrook et al. (Sambrook et al., *Molecular Cloning: A Laboratory Manual*, Spring Harbor, N.Y., 1989), incorporated herein by reference. Such systems may be used to express cis-ZOG1 at high levels to facilitate purification of the enzyme. The enzyme may be used for a variety of purposes. For example, the enzyme may be applied directly to plants to modulate zeatin function. Alternatively the purified enzyme produced by recombinant means may be used to synthesize other zeatin metabolites in vitro, particularly radio- or fluorescent-labeled forms of cis-O-glucosylzeatin. These molecules may be used as tracers to determine the location in plant tissues and cells of zeatin and its metabolites. In addition, the recombinant form of the enzyme may be used to produce labeled forms of metabolites of other substrates (for example, isoprenylated proteins) on which it may act. The purified recombinant enzyme may also be used as an immunogen to raise enzyme-specific antibodies. Such antibodies are useful as research reagents (such as in the study of cytokinin regulation in plants) and can be used diagnostically to determine expression levels of the enzyme in agricultural products, including seed.

By way of example only, high-level expression of the cis-ZOG1-protein may be achieved by cloning and expressing the cDNA in yeast cells using the pYES2 yeast-expression vector (InVitrogen, San Diego, Calif.). The recombinant cis-ZOG1 may be supplied in the harvested yeast cells (for subsequent processing). Alternatively, a genetic construct may be produced to direct secretion of the recombinant cis-ZOG1 from the yeast cells into the medium. This approach will facilitate the purification of the cis-ZOG1, if necessary. Secretion of the recombinant cis-ZOG1 from the yeast cells may be achieved by placing a yeast-signal sequence adjacent to the cis-ZOG1 coding region. A number of yeast-signal sequences have been characterized, including the signal sequence for yeast invertase. This sequence has been successfully used to direct the secretion of heterologous proteins from yeast cells, including proteins such as human interferon (Chang et al., *Mol. and Cell. Biol.* 6:1812–1819, 1986), human lactoferrin (Liang et al., *J. Agric. Food Chem.* 41:1800–1807, 1993), and prochymosin (Smith et al., *Science* 229:1219–1224, 1985).

Alternatively, the enzyme may be expressed at high level in prokaryotic expression systems, such as *E. coli* as described above.

Having illustrated and described the principles of the disclosure in multiple embodiments and examples, it should be apparent to those skilled in the art that the provided compositions and methods can be modified in arrangement and detail without departing from such principles. We claim all modifications coming within the spirit and scope of the following claims.

We claim:

1. An isolated nucleic acid molecule, comprising:
a nucleic acid sequence which encodes a polypeptide comprising the amino acid sequence of SEQ ID NO: 8, wherein the nucleic acid molecule encodes a polypeptide that catalyzes the conversion of cis-zeatin to cis-O-glucosylzeatin.

2. The isolated nucleic acid molecule of claim 1, wherein the nucleic acid sequence comprises the nucleic acid sequence set forth in SEQ ID NO: 7, SEQ ID NO: 11, or a nucleic acid sequence that differs from SEQ ID NO: 7 or SEQ ID NO: 11 by virtue of the degeneracy of the genetic code without affecting the amino acid composition of the encoded protein.

3. The isolated nucleic acid molecule of claim 2, wherein the nucleic acid sequence is the nucleic acid sequence as set forth in SEQ ID NO: 7 or SEQ ID NO: 11.

4. A recombinant nucleic acid molecule, comprising a promoter sequence operably linked to the nucleic acid molecule of claim 1.

5. A transgenic plant, comprising the recombinant nucleic acid molecule of claim 4.

* * * * *

UNITED STATES PATENT AND TRADEMARK OFFICE
CERTIFICATE OF CORRECTION

| | |
|---|---|
| PATENT NO. | : 7,148,405 B2 |
| APPLICATION NO. | : 10/275782 |
| DATED | : December 12, 2006 |
| INVENTOR(S) | : Mok et al. |

Page 1 of 1

It is certified that error appears in the above-identified patent and that said Letters Patent is hereby corrected as shown below:

<u>On the Cover, item [54]:</u>

In the title, "ENZYMES RESPONSIBLE FOR THE METABOLISM OF CIS-ZEATIN" should be --CIS-ZEATIN O-GLUCOSYLTRANSFERASE FROM ZEA MAYS--.

Column 1, line 59, "set" should be --set.--.

Column 2, line 2, "gram" should be --grain--.

Column 3, line 5, "action:" should be --action--.

Column 6, line 36, "cytokinln" should be --cytokinin--.

Column 6, line 62, "organeue" should be --organelle--.

Column 9, line 56, "Poly A Ttract" should be --PolyATtract--.

Column 10, lines 9-10, "p Trc 99A" should be --pTrc99A--.

Column 11, line 8, "ampl" should be --amplify--.

Column 19, line 10, "log $_{10}$" should be --log$_{10}$--.

Signed and Sealed this

Tenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,148,405 B2  Page 1 of 1
APPLICATION NO. : 10/275782
DATED : December 12, 2006
INVENTOR(S) : Mok et al.

It is certified that error appears in the above-identified patent and that said Letters Patent is hereby corrected as shown below:

On the Cover, item [54] and Column 1, lines 1 and 2:

In the title, "ENZYMES RESPONSIBLE FOR THE METABOLISM OF CIS-ZEATIN" should be --CIS-ZEATIN O-GLUCOSYLTRANSFERASE FROM ZEA MAYS--.

Column 1, line 59, "set" should be --set.--.

Column 2, line 2, "gram" should be --grain--.

Column 3, line 5, "action:" should be --action--.

Column 6, line 36, "cytokinln" should be --cytokinin--.

Column 6, line 62, "organeue" should be --organelle--.

Column 9, line 56, "Poly A Ttract" should be --PolyATtract--.

Column 10, lines 9-10, "p Trc 99A" should be --pTrc99A--.

Column 11, line 8, "ampl" should be --amplify--.

Column 19, line 10, "log $_{10}$" should be --log$_{10}$--.

This certificate supersedes the Certificate of Correction issued June 10, 2008.

Signed and Sealed this

Fifteenth Day of July, 2008

JON W. DUDAS
*Director of the United States Patent and Trademark Office*

SEQUENCE LISTING

<160> NUMBER OF SEQ ID NOS: 11

<210> SEQ ID NO 1
<211> LENGTH: 1380
<212> TYPE: DNA

<213> ORGANISM: Phaseolus lunatus
<220> FEATURE:
<221> NAME/KEY: CDS
<222> LOCATION: (1)..(1380)
<223> OTHER INFORMATION:

<400> SEQUENCE: 1

```
atg gct ttg aat gac aaa agc att cct cat gaa acc aaa gtg gtg gtg      48
Met Ala Leu Asn Asp Lys Ser Ile Pro His Glu Thr Lys Val Val Val
1               5                   10                  15 ctt ttg ata cct ttc cct gca caa ggt cac ctc aac cag ttt ctg cac      96
Leu Leu Ile Pro Phe Pro Ala Gln Gly His Leu Asn Gln Phe Leu His
                20                  25                  30 cta tct cgc tta atc gtg gca caa aac ata cca gtc cat tat gtt ggc     144
Leu Ser Arg Leu Ile Val Ala Gln Asn Ile Pro Val His Tyr Val Gly
            35                  40                  45 act gtc aca cac att cgc cag gca aca ctt cga tac aac aac cct act     192
Thr Val Thr His Ile Arg Gln Ala Thr Leu Arg Tyr Asn Asn Pro Thr
        50                  55                  60 tca aac atc cat ttc cat gcc ttt caa gtt cca ccc ttt gtt tcc cct     240
Ser Asn Ile His Phe His Ala Phe Gln Val Pro Pro Phe Val Ser Pro
65                  70                  75                  80 cct ccc aat cca gaa gac gat ttc cca tct cat cta att cct tcc ttt     288
Pro Pro Asn Pro Glu Asp Asp Phe Pro Ser His Leu Ile Pro Ser Phe
                85                  90                  95 gag gcc tct gca cac ctt cgg gag ccc gtg ggg aaa ctt ctt caa tcc     336
Glu Ala Ser Ala His Leu Arg Glu Pro Val Gly Lys Leu Leu Gln Ser
                100                 105                 110 ctc tca tca caa gcc aaa agg gtc gta gtc atc aat gac tcc ctc atg     384
Leu Ser Ser Gln Ala Lys Arg Val Val Val Ile Asn Asp Ser Leu Met
            115                 120                 125 gca tct gtg gca caa gat gcc gca aac atc tca aat gtt gaa aac tac     432
Ala Ser Val Ala Gln Asp Ala Ala Asn Ile Ser Asn Val Glu Asn Tyr
        130                 135                 140 act ttt cac agc ttc tct gcc ttt aat acc tcc ggt gat ttt tgg gaa     480
Thr Phe His Ser Phe Ser Ala Phe Asn Thr Ser Gly Asp Phe Trp Glu
145                 150                 155                 160 gaa atg gga aag ccc ccg gtt gga gat ttc cat ttc cca gaa ttt cct     528
Glu Met Gly Lys Pro Pro Val Gly Asp Phe His Phe Pro Glu Phe Pro
                165                 170                 175 tct ctt gaa gga tgc atc gca gcc cag ttc aag ggc ttt cgt act gca     576
Ser Leu Glu Gly Cys Ile Ala Ala Gln Phe Lys Gly Phe Arg Thr Ala
                180                 185                 190 cag tat gaa ttc cgc aaa ttc aac aat ggc gat att tac aac acc agc     624
Gln Tyr Glu Phe Arg Lys Phe Asn Asn Gly Asp Ile Tyr Asn Thr Ser
            195                 200                 205 agg gtg att gaa ggt cct tac gtt gag ttg ctg gag ctt ttc aat ggc     672
Arg Val Ile Glu Gly Pro Tyr Val Glu Leu Leu Glu Leu Phe Asn Gly
        210                 215                 220 ggc aag aag gtt tgg gca ttg ggg cca ttt aac cct tta gcc gtt gag     720
Gly Lys Lys Val Trp Ala Leu Gly Pro Phe Asn Pro Leu Ala Val Glu
225                 230                 235                 240 aag aaa gat tca ata gga ttt agg cac cca tgc atg gag tgg ctt gat     768
Lys Lys Asp Ser Ile Gly Phe Arg His Pro Cys Met Glu Trp Leu Asp
                245                 250                 255 aaa caa gag cca agt tca gtc ata tat ata tcc ttc ggg acc acg aca     816
Lys Gln Glu Pro Ser Ser Val Ile Tyr Ile Ser Phe Gly Thr Thr Thr
                260                 265                 270 gct ttg aga gat gaa caa atc caa cag ata gca act ggg ttg gaa caa     864
Ala Leu Arg Asp Glu Gln Ile Gln Gln Ile Ala Thr Gly Leu Glu Gln
            275                 280                 285
```

```
agc aag cag aag ttc atc tgg gtg ctg aga gaa gcc gat aaa ggg gac    912
Ser Lys Gln Lys Phe Ile Trp Val Leu Arg Glu Ala Asp Lys Gly Asp
    290                 295                 300 atc ttt gcc gga agt gaa gca aaa agg tat gaa ctt cca aag ggt ttt    960
Ile Phe Ala Gly Ser Glu Ala Lys Arg Tyr Glu Leu Pro Lys Gly Phe
305                 310                 315                 320 gag gag aga gtg gaa gga atg ggg ctg gtt gtg agg gac tgg gca ccc   1008
Glu Glu Arg Val Glu Gly Met Gly Leu Val Val Arg Asp Trp Ala Pro
                325                 330                 335 caa ttg gaa att ctg agc cac agt tca aca ggg ggg ttt atg agc cat   1056
Gln Leu Glu Ile Leu Ser His Ser Ser Thr Gly Gly Phe Met Ser His
            340                 345                 350 tgt gga tgg aac tcg tgc ttg gag agc ata acc atg ggg gtg cca ata   1104
Cys Gly Trp Asn Ser Cys Leu Glu Ser Ile Thr Met Gly Val Pro Ile
        355                 360                 365 gca aca tgg ccc atg cac tct gac cag cca aga aat gca gtt ttg gtt   1152
Ala Thr Trp Pro Met His Ser Asp Gln Pro Arg Asn Ala Val Leu Val
    370                 375                 380 aca gag gtt ctg aag gtt ggt ttg gtt gtg aag gat tgg gca cag agg   1200
Thr Glu Val Leu Lys Val Gly Leu Val Val Lys Asp Trp Ala Gln Arg
385                 390                 395                 400 aat tcg ttg gtg agt gct tca gtt gtt gag aat ggt gtg aga agg ttg   1248
Asn Ser Leu Val Ser Ala Ser Val Val Glu Asn Gly Val Arg Arg Leu
                405                 410                 415 atg gaa aca aag gaa ggt gat gag atg aga cag aga gca gtg agg ctt   1296
Met Glu Thr Lys Glu Gly Asp Glu Met Arg Gln Arg Ala Val Arg Leu
            420                 425                 430 aaa aat gcc atc cat agg tca atg gat gaa ggt gga gtt tct cac atg   1344
Lys Asn Ala Ile His Arg Ser Met Asp Glu Gly Gly Val Ser His Met
        435                 440                 445 gag atg ggt tct ttc att gca cac atc tct aaa tag                   1380
Glu Met Gly Ser Phe Ile Ala His Ile Ser Lys
    450                 455

<210> SEQ ID NO 2
<211> LENGTH: 459
<212> TYPE: PRT
<213> ORGANISM: Phaseolus lunatus

<400> SEQUENCE: 2

Met Ala Leu Asn Asp Lys Ser Ile Pro His Glu Thr Lys Val Val
1               5                   10                  15

Leu Leu Ile Pro Phe Pro Ala Gln Gly His Leu Asn Gln Phe Leu His
                20                  25                  30

Leu Ser Arg Leu Ile Val Ala Gln Asn Ile Pro Val His Tyr Val Gly
            35                  40                  45

Thr Val Thr His Ile Arg Gln Ala Thr Leu Arg Tyr Asn Asn Pro Thr
        50                  55                  60

Ser Asn Ile His Phe His Ala Phe Gln Val Pro Phe Val Ser Pro
65                  70                  75                  80

Pro Pro Asn Pro Glu Asp Asp Phe Pro Ser His Leu Ile Pro Ser Phe
                85                  90                  95

Glu Ala Ser Ala His Leu Arg Glu Pro Val Gly Lys Leu Leu Gln Ser
            100                 105                 110

Leu Ser Ser Gln Ala Lys Arg Val Val Ile Asn Asp Ser Leu Met
        115                 120                 125

Ala Ser Val Ala Gln Asp Ala Ala Asn Ile Ser Asn Val Glu Asn Tyr
    130                 135                 140
```

-continued

```
Thr Phe His Ser Phe Ser Ala Phe Asn Thr Ser Gly Asp Phe Trp Glu
145                 150                 155                 160

Glu Met Gly Lys Pro Pro Val Gly Asp Phe His Phe Pro Glu Phe Pro
                165                 170                 175

Ser Leu Glu Gly Cys Ile Ala Ala Gln Phe Lys Gly Phe Arg Thr Ala
            180                 185                 190

Gln Tyr Glu Phe Arg Lys Phe Asn Asn Gly Asp Ile Tyr Asn Thr Ser
        195                 200                 205

Arg Val Ile Glu Gly Pro Tyr Val Glu Leu Leu Glu Leu Phe Asn Gly
    210                 215                 220

Gly Lys Lys Val Trp Ala Leu Gly Pro Phe Asn Pro Leu Ala Val Glu
225                 230                 235                 240

Lys Lys Asp Ser Ile Gly Phe Arg His Pro Cys Met Glu Trp Leu Asp
                245                 250                 255

Lys Gln Glu Pro Ser Ser Val Ile Tyr Ile Ser Phe Gly Thr Thr Thr
                260                 265                 270

Ala Leu Arg Asp Glu Gln Ile Gln Gln Ile Ala Thr Gly Leu Glu Gln
            275                 280                 285

Ser Lys Gln Lys Phe Ile Trp Val Leu Arg Glu Ala Asp Lys Gly Asp
        290                 295                 300

Ile Phe Ala Gly Ser Glu Ala Lys Arg Tyr Glu Leu Pro Lys Gly Phe
305                 310                 315                 320

Glu Glu Arg Val Glu Gly Met Gly Leu Val Val Arg Asp Trp Ala Pro
                325                 330                 335

Gln Leu Glu Ile Leu Ser His Ser Ser Thr Gly Gly Phe Met Ser His
            340                 345                 350

Cys Gly Trp Asn Ser Cys Leu Glu Ser Ile Thr Met Gly Val Pro Ile
        355                 360                 365

Ala Thr Trp Pro Met His Ser Asp Gln Pro Arg Asn Ala Val Leu Val
    370                 375                 380

Thr Glu Val Leu Lys Val Gly Leu Val Val Lys Asp Trp Ala Gln Arg
385                 390                 395                 400

Asn Ser Leu Val Ser Ala Ser Val Val Glu Asn Gly Val Arg Arg Leu
                405                 410                 415

Met Glu Thr Lys Glu Gly Asp Glu Met Arg Gln Arg Ala Val Arg Leu
            420                 425                 430

Lys Asn Ala Ile His Arg Ser Met Asp Glu Gly Gly Val Ser His Met
        435                 440                 445

Glu Met Gly Ser Phe Ile Ala His Ile Ser Lys
    450                 455

<210> SEQ ID NO 3
<211> LENGTH: 187
<212> TYPE: DNA
<213> ORGANISM: Zea mays

<400> SEQUENCE: 3
ctacgtctcg ttcggcacga cttcgtgcct ccacgccgac caagtcgccg agctcgccgc      60
ggcgctcaag ggcagcaagc agcgtttcgt ctgggtgctg cgcgacgccg accgcgccaa     120
catatacgcc gagtccggcg agagccggca cgccatgttc ctgtccgagt tcaccagagg     180
agaccga                                                               187

<210> SEQ ID NO 4
```

-continued

```
<211> LENGTH: 24
<212> TYPE: DNA
<213> ORGANISM: artificial sequence
<220> FEATURE:
<223> OTHER INFORMATION: Synthetic oligonucleotide primer

<400> SEQUENCE: 4
ctacgtctcg ttcggcacga cttc                                                24

<210> SEQ ID NO 5
<211> LENGTH: 24
<212> TYPE: DNA
<213> ORGANISM: artificial sequence
<220> FEATURE:
<223> OTHER INFORMATION: Synthetic oligonucleotide primer

<400> SEQUENCE: 5
cagcgtggag ttccaaccgc agtg                                                24

<210> SEQ ID NO 6
<211> LENGTH: 292
<212> TYPE: DNA
<213> ORGANISM: Zea mays

<400> SEQUENCE: 6
ctacgtctcg ttcggcacga cttcgtcgct gcgggcggag cagatcgcag aactcgccgc         60
ggcgctgcgc gacagcaaac agcggttcgt ctgggttctg cacgacgctg atcgcggtgt        120
ggtacgcgag gaggaagccg tggagagtag gcactccagg ttcctatccg agttcaccga        180
ggaaactcaa ggcatcgggt tggtgatcac cgggtgggcg ccgcagttgg agatcctggc        240
ccacggcgcc acggcagcgt tcatgagtca ctgcggttgg aactccacgc tg                292

<210> SEQ ID NO 7
<211> LENGTH: 1404
<212> TYPE: DNA
<213> ORGANISM: Zea mays
<220> FEATURE:
<221> NAME/KEY: CDS
<222> LOCATION: (1)..(1404)
<223> OTHER INFORMATION:

<400> SEQUENCE: 7 atg gcg gtt gac acg atg gag tcg gtt gcc gtc gtg gcc gtg ccg ttc          48
Met Ala Val Asp Thr Met Glu Ser Val Ala Val Val Ala Val Pro Phe
1               5                   10                  15 ccg gcg cag ggc cat ctg aac cag ctg ctc cac ctg tcg ctg ctg ctg          96
Pro Ala Gln Gly His Leu Asn Gln Leu Leu His Leu Ser Leu Leu Leu
            20                  25                  30 gcg tcg cgg ggg ctg tcc gtg cac tac gcg gcg ccc ccg cac gtc               144
Ala Ser Arg Gly Leu Ser Val His Tyr Ala Ala Pro Pro His Val
        35                  40                  45 cgc cag gcg cgc gcg cgc gtg cac ggc tgg gac ccc agg gcg ctc ggc          192
Arg Gln Ala Arg Ala Arg Val His Gly Trp Asp Pro Arg Ala Leu Gly
    50                  55                  60 tcc atc cgc ttc cac gac ctc gac gtc cca ccg tac gac tcc ccc gcg          240
Ser Ile Arg Phe His Asp Leu Asp Val Pro Pro Tyr Asp Ser Pro Ala
65                  70                  75                  80 ccg gac ctg gcc gcg ccg tcg ccg ttc ccg aac cac ctc atg ccc atg          288
Pro Asp Leu Ala Ala Pro Ser Pro Phe Pro Asn His Leu Met Pro Met
                85                  90                  95 ttc gag gcc ttc gcc gcc gcg gcg cgc gcc ccg ctc gcg gcc ctc ctc          336
Phe Glu Ala Phe Ala Ala Ala Ala Arg Ala Pro Leu Ala Ala Leu Leu
            100                 105                 110
```

| | | |
|---|---|---|
| cag cgc ctg tcc acc agc tac cgc cgc gtg gcc gtc gtc ttc gac cgc<br>Gln Arg Leu Ser Thr Ser Tyr Arg Arg Val Ala Val Val Phe Asp Arg<br>115                      120                      125 | | 384 |
| ctc aac ccc ttc gcc gcc acg gag gcg gcg cgg ctg gcc aac gcc gac<br>Leu Asn Pro Phe Ala Ala Thr Glu Ala Ala Arg Leu Ala Asn Ala Asp<br>130                      135                      140 | | 432 |
| gcg ttc ggc ctg cag tgc gtc gcc atc tcg tac aac gtt ggg tgg ctg<br>Ala Phe Gly Leu Gln Cys Val Ala Ile Ser Tyr Asn Val Gly Trp Leu<br>145                      150                      155                      160 | | 480 |
| gac ccg ggc cac cgc ctc ctc agc gac tac ggc ctc cag ttc ctg ccc<br>Asp Pro Gly His Arg Leu Leu Ser Asp Tyr Gly Leu Gln Phe Leu Pro<br>                  165                      170                      175 | | 528 |
| ccc gac gcc tgc atg tcc agg gag ttc gtg gac ctc gtc ttc cgg atg<br>Pro Asp Ala Cys Met Ser Arg Glu Phe Val Asp Leu Val Phe Arg Met<br>                180                      185                      190 | | 576 |
| gag gag gag gag cag ggc gcg ccc gtc gcc ggc ttg gtc atg aac acg<br>Glu Glu Glu Glu Gln Gly Ala Pro Val Ala Gly Leu Val Met Asn Thr<br>195                      200                      205 | | 624 |
| tgc cgc gcg ctg gag ggc gag ttc ctc gac gtg gtc gcc gcg cag ccg<br>Cys Arg Ala Leu Glu Gly Glu Phe Leu Asp Val Val Ala Ala Gln Pro<br>210                      215                      220 | | 672 |
| ccg ttc caa ggc cag agg ttc ttc gcg gtc ggc ccg ctc aac ccg ctc<br>Pro Phe Gln Gly Gln Arg Phe Phe Ala Val Gly Pro Leu Asn Pro Leu<br>225                      230                      235                      240 | | 720 |
| ctg ctc gat gcg gac gcc ccg acg acg ccg ccg ggg cag gcg cgg cac<br>Leu Leu Asp Ala Asp Ala Pro Thr Thr Pro Pro Gly Gln Ala Arg His<br>                  245                      250                      255 | | 768 |
| gag tgc ctg gag tgg ctc gac agg cag ccg ccg gag tcg gtg ctc tac<br>Glu Cys Leu Glu Trp Leu Asp Arg Gln Pro Pro Glu Ser Val Leu Tyr<br>        260                      265                      270 | | 816 |
| gtc tcg ttc ggc acg act tcg tgc ctc cac gcc gac caa gtc gcc gag<br>Val Ser Phe Gly Thr Thr Ser Cys Leu His Ala Asp Gln Val Ala Glu<br>275                      280                      285 | | 864 |
| ctc gcc gcg gcg ctc aag ggc agc aag cag cgt ttc gtc tgg gtg ctg<br>Leu Ala Ala Ala Leu Lys Gly Ser Lys Gln Arg Phe Val Trp Val Leu<br>290                      295                      300 | | 912 |
| cgc gac gcc gac cgc gcc gac ata tac gcc gag tcc ggc gag agc cgg<br>Arg Asp Ala Asp Arg Ala Asp Ile Tyr Ala Glu Ser Gly Glu Ser Arg<br>305                      310                      315                      320 | | 960 |
| cac gcc atg ttc ctg tcc gag ttc acc agg gag acc gag ggc acg ggg<br>His Ala Met Phe Leu Ser Glu Phe Thr Arg Glu Thr Glu Gly Thr Gly<br>                  325                      330                      335 | | 1008 |
| ctg gtc atc acc ggg tgg gcg ccg cag ctg gag atc ctg gcg cac ggc<br>Leu Val Ile Thr Gly Trp Ala Pro Gln Leu Glu Ile Leu Ala His Gly<br>        340                      345                      350 | | 1056 |
| gcc acg gcg gcc ttc atg agc cac tgc ggc tgg aac tcg acc atc gag<br>Ala Thr Ala Ala Phe Met Ser His Cys Gly Trp Asn Ser Thr Ile Glu<br>355                      360                      365 | | 1104 |
| agc ctg agc cac ggg aag ccg gtg ctt gcc tgg ccc atg cac tcc gac<br>Ser Leu Ser His Gly Lys Pro Val Leu Ala Trp Pro Met His Ser Asp<br>370                      375                      380 | | 1152 |
| cag ccg tgg gac tcg gag ctt ctg tgc aag tac ttc aag gca ggg ctc<br>Gln Pro Trp Asp Ser Glu Leu Leu Cys Lys Tyr Phe Lys Ala Gly Leu<br>385                      390                      395                      400 | | 1200 |
| ctg gtc agg ccc tgg gag aaa cac gct gaa atc gta ccg gcg cag gcc<br>Leu Val Arg Pro Trp Glu Lys His Ala Glu Ile Val Pro Ala Gln Ala<br>                  405                      410                      415 | | 1248 |
| atc caa aag gtg atc gag gag gca atg cta tcc gac agc ggg atg gcg<br>Ile Gln Lys Val Ile Glu Glu Ala Met Leu Ser Asp Ser Gly Met Ala | | 1296 |

```
                420              425              430
gtg cgg cag cgg gcc aag gag ctc ggg gag gcg gtt cgc gcc tcc gtg    1344
Val Arg Gln Arg Ala Lys Glu Leu Gly Glu Ala Val Arg Ala Ser Val
            435              440              445 gct gac ggc ggg aac tcg cgt aag gat ctc gac gat ttc att ggc tac    1392
Ala Asp Gly Gly Asn Ser Arg Lys Asp Leu Asp Asp Phe Ile Gly Tyr
450              455              460 atc aca agg tga                                                    1404
Ile Thr Arg
465

<210> SEQ ID NO 8
<211> LENGTH: 467
<212> TYPE: PRT
<213> ORGANISM: Zea mays

<400> SEQUENCE: 8

Met Ala Val Asp Thr Met Glu Ser Val Ala Val Ala Val Pro Phe
1               5                  10                  15

Pro Ala Gln Gly His Leu Asn Gln Leu Leu His Leu Ser Leu Leu Leu
                20                  25                  30

Ala Ser Arg Gly Leu Ser Val His Tyr Ala Ala Pro Pro His Val
            35                  40                  45

Arg Gln Ala Arg Ala Arg Val His Gly Trp Asp Pro Arg Ala Leu Gly
    50                  55                  60

Ser Ile Arg Phe His Asp Leu Asp Val Pro Pro Tyr Asp Ser Pro Ala
65                  70                  75                  80

Pro Asp Leu Ala Ala Pro Ser Pro Phe Pro Asn His Leu Met Pro Met
                85                  90                  95

Phe Glu Ala Phe Ala Ala Ala Arg Ala Pro Leu Ala Ala Leu Leu
            100                 105                 110

Gln Arg Leu Ser Thr Ser Tyr Arg Arg Val Ala Val Phe Asp Arg
        115                 120                 125

Leu Asn Pro Phe Ala Ala Thr Glu Ala Ala Arg Leu Ala Asn Ala Asp
    130                 135                 140

Ala Phe Gly Leu Gln Cys Val Ala Ile Ser Tyr Asn Val Gly Trp Leu
145                 150                 155                 160

Asp Pro Gly His Arg Leu Leu Ser Asp Tyr Gly Leu Gln Phe Leu Pro
                165                 170                 175

Pro Asp Ala Cys Met Ser Arg Glu Phe Val Asp Leu Val Phe Arg Met
            180                 185                 190

Glu Glu Glu Glu Gln Gly Ala Pro Val Ala Gly Leu Val Met Asn Thr
        195                 200                 205

Cys Arg Ala Leu Glu Gly Glu Phe Leu Asp Val Val Ala Ala Gln Pro
    210                 215                 220

Pro Phe Gln Gly Gln Arg Phe Ala Val Gly Pro Leu Asn Pro Leu
225                 230                 235                 240

Leu Leu Asp Ala Asp Ala Pro Thr Thr Pro Pro Gly Gln Ala Arg His
                245                 250                 255

Glu Cys Leu Glu Trp Leu Asp Arg Gln Pro Pro Glu Ser Val Leu Tyr
            260                 265                 270

Val Ser Phe Gly Thr Thr Ser Cys Leu His Ala Asp Gln Val Ala Glu
        275                 280                 285

Leu Ala Ala Ala Leu Lys Gly Ser Lys Gln Arg Phe Val Trp Val Leu
    290                 295                 300
```

```
Arg Asp Ala Asp Arg Ala Asp Ile Tyr Ala Glu Ser Gly Glu Ser Arg
305                 310                 315                 320

His Ala Met Phe Leu Ser Glu Phe Thr Arg Glu Thr Glu Gly Thr Gly
            325                 330                 335

Leu Val Ile Thr Gly Trp Ala Pro Gln Leu Glu Ile Leu Ala His Gly
        340                 345                 350

Ala Thr Ala Ala Phe Met Ser His Cys Gly Trp Asn Ser Thr Ile Glu
        355                 360                 365

Ser Leu Ser His Gly Lys Pro Val Leu Ala Trp Pro Met His Ser Asp
    370                 375                 380

Gln Pro Trp Asp Ser Glu Leu Leu Cys Lys Tyr Phe Lys Ala Gly Leu
385                 390                 395                 400

Leu Val Arg Pro Trp Glu Lys His Ala Glu Ile Val Pro Ala Gln Ala
                405                 410                 415

Ile Gln Lys Val Ile Glu Glu Ala Met Leu Ser Asp Ser Gly Met Ala
            420                 425                 430

Val Arg Gln Arg Ala Lys Glu Leu Gly Glu Ala Val Arg Ala Ser Val
        435                 440                 445

Ala Asp Gly Gly Asn Ser Arg Lys Asp Leu Asp Asp Phe Ile Gly Tyr
    450                 455                 460

Ile Thr Arg
465

<210> SEQ ID NO 9
<211> LENGTH: 31
<212> TYPE: DNA
<213> ORGANISM: Zea mays

<400> SEQUENCE: 9
gagctaaccc atggcggttg acacgatgga g                              31

<210> SEQ ID NO 10
<211> LENGTH: 33
<212> TYPE: DNA
<213> ORGANISM: artificial sequence
<220> FEATURE:
<223> OTHER INFORMATION: Synthetic oligonucleotide primer

<400> SEQUENCE: 10
catgcgtcta gatactttca ccttgtgatg tag                            33

<210> SEQ ID NO 11
<211> LENGTH: 1553
<212> TYPE: DNA
<213> ORGANISM: Zea mays

<400> SEQUENCE: 11
ctcacgttgt cactcataca cacccgagct gagctaacta atggcggttg acacgatgga      60
gtcggttgcc gtcgtggccg tgccgttccc ggcgcagggc catctgaacc agctgctcca     120
cctgtcgctg ctgctggcgt cgcgggggct gtccgtgcac tacgcggcgc cccgccgca     180 cgtccgccag gcgcgcgcgc gcgtgcacgg ctgggacccc agggcgctcg gctccatccg     240
cttccacgac ctcgacgtcc caccgtacga ctcccccgcg ccggacctgg ccgcgccgtc     300
gccgttcccg aaccacctca tgcccatgtt cgaggccttc gccgccgcgg cgcgcgcccc     360
gctcgcggcc ctcctccagc gcctgtccac cagctaccgc cgcgtggccg tcgtcttcga     420
ccgcctcaac cccttcgccg ccacggaggc ggcgcggctg gccaacgccg acgcgttcgg     480
```

```
cctgcagtgc gtcgccatct cgtacaacgt tgggtggctg gacccgggcc accgcctcct     540
cagcgactac ggcctccagt tcctgccccc cgacgcctgc atgtccaggg agttcgtgga     600
cctcgtcttc cggatggagg aggaggagca gggcgcgccc gtcgccggct tggtcatgaa     660
cacgtgccgc gcgctggagg gcgagttcct cgacgtggtc gccgcgcagc cgccgttcca     720
aggccagagg ttcttcgcgg tcggcccgct caacccgctc ctgctcgatg cggacgcccc     780
gacgacgccg ccggggcagg cgcggcacga gtgcctggag tggctcgaca ggcagccgcc     840
ggagtcggtg ctctacgtct cgttcggcac gacttcgtgc ctccacgccg accaagtcgc     900
cgagctcgcc gcggcgctca agggcagcaa gcagcgtttc gtctgggtgc tgcgcgacgc     960
cgaccgcgcc gacatatacg ccgagtccgg cgagagccgg cacgccatgt tcctgtccga    1020
gttcaccagg gagaccgagg gcacggggct ggtcatcacc gggtgggcgc cgcagctgga    1080
gatcctggcg cacggcgcca cggcggcctt catgagccac tgcggctgga actcgaccat    1140
cgagagcctg agccacggga agccggtgct tgcctggccc atgcactccg accagccgtg    1200
ggactcggag cttctgtgca agtacttcaa ggcagggctc ctggtcaggc cctgggagaa    1260
acacgctgaa atcgtaccgg cgcaggccat ccaaaaggtg atcgaggagg caatgctatc    1320
cgacagcggg atggcggtgc ggcagcgggc caaggagctc ggggaggcgg ttcgcgcctc    1380
cgtggctgac ggcgggaact cgcgtaagga tctcgacgat ttcattggct acatcacaag    1440
gtgaaagtat gacgacgcat gggggatata gaaaatcatc tgctgctttc agcggttaat    1500
cggataactt tgaatcgtcc acagaaaata aaatattac tgtcgaaatt ttc            1553
```